(12) United States Patent
Wermeling et al.

(10) Patent No.: US 6,948,492 B2
(45) Date of Patent: Sep. 27, 2005

(54) PROGRAMMABLE MULTI-DOSE INTRANASAL DRUG DELIVERY DEVICE

(75) Inventors: Daniel P. Wermeling, Lexington, KY (US); Ryan Vallance, Lexington, KY (US); Aravind Balasubramaniam, Lexington, KY (US); Bruce Lanier Walcott, Lexington, KY (US); John Alan Main, Lexington, KY (US); James E. Lumpp, Jr., Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 175 days.

(21) Appl. No.: 10/129,578

(22) PCT Filed: Aug. 15, 2001

(86) PCT No.: PCT/US01/25726

§ 371 (c)(1),
(2), (4) Date: Mar. 20, 2003

(87) PCT Pub. No.: WO02/13886

PCT Pub. Date: Feb. 21, 2002

(65) Prior Publication Data

US 2003/0163099 A1 Aug. 28, 2003

Related U.S. Application Data

(60) Provisional application No. 60/225,624, filed on Aug. 15, 2000.

(51) Int. Cl.[7] .............................................. A61M 11/00
(52) U.S. Cl. ............................ 128/200.14; 128/200.17; 128/203.15; 128/203.21
(58) Field of Search ........................ 128/200.14, 200.17, 128/200.23, 203.15, 203.23, 203.21

(56) References Cited

U.S. PATENT DOCUMENTS

| | | | |
|---|---|---|---|
| 3,812,853 A | | 5/1974 | Crain |
| 4,464,378 A | | 8/1984 | Hussain |
| 4,627,432 A | * | 12/1986 | Newell et al. ......... 128/203.15 |
| 4,673,679 A | | 6/1987 | Aungst et al. |
| 4,782,047 A | | 11/1988 | Benjamin et al. |
| 4,889,860 A | | 12/1989 | Rzeszotarski |
| 4,946,069 A | | 8/1990 | Fuchs |
| 4,950,664 A | | 8/1990 | Goldberg |
| 4,973,596 A | | 11/1990 | Cohen |
| 5,035,237 A | * | 7/1991 | Newell et al. ......... 128/203.15 |
| 5,132,114 A | | 7/1992 | Stanley et al. |
| 5,169,029 A | | 12/1992 | Behar et al. |
| 5,207,217 A | * | 5/1993 | Cocozza et al. ....... 128/203.21 |

(Continued)

FOREIGN PATENT DOCUMENTS

| | | |
|---|---|---|
| WO | WO 90/02737 | 3/1990 |
| WO | WO 02/11778 A1 | 2/2002 |

*Primary Examiner*—Glenn K. Dawson
*Assistant Examiner*—Darwin P. Erezo
(74) *Attorney, Agent, or Firm*—Mayer Brown Rowe & Maw LLP

(57) ABSTRACT

An apparatus and method for the self-administration of a plurality of doses of an intranasal liquid pharmaceutical composition, including opioid analgesics, that includes a drug delivery device containing a plurality of sealed vials, each vial containing a predetermined volume of the pharmaceutical composition, a pump assembly for conveying the liquid pharmaceutical composition from the interior of the vial and discharging it as a nasal spray in response to manual activation by the patient, and programmable means for sequentially advancing a vial to the ready position after passage of a prescribed time interval following the last activation of the delivery device.

47 Claims, 21 Drawing Sheets

U.S. PATENT DOCUMENTS

| | | |
|---|---|---|
| 5,225,183 A | 7/1993 | Purewal et al. |
| 5,307,953 A | 5/1994 | Regan |
| 5,397,771 A | 3/1995 | Bechgaard et al. |
| 5,428,006 A | 6/1995 | Bechgaard et al. |
| 5,492,112 A * | 2/1996 | Mecikalski et al. .... 128/203.15 |
| 5,529,787 A | 6/1996 | Merrill et al. |
| 5,543,434 A | 8/1996 | Weg |
| 5,577,497 A | 11/1996 | Mecikalski et al. |
| 5,622,163 A | 4/1997 | Jewett et al. |
| 5,622,166 A * | 4/1997 | Eisele et al. ........... 128/203.12 |
| 5,629,011 A | 5/1997 | Illum |
| 5,637,314 A | 6/1997 | Sharpe et al. |
| 5,683,677 A | 11/1997 | Purewal et al. |
| 5,693,608 A | 12/1997 | Bechgaard et al. |
| 5,695,743 A | 12/1997 | Purewal et al. |
| 5,702,725 A | 12/1997 | Merrill et al. |
| 5,766,573 A | 6/1998 | Purewal et al. |
| 5,866,143 A | 2/1999 | Elkhoury |
| 5,921,237 A * | 7/1999 | Eisele et al. ........... 128/203.21 |
| 5,948,389 A | 9/1999 | Stein |
| 5,958,379 A | 9/1999 | Regenold |
| 6,015,797 A | 1/2000 | Camborde et al. |
| 6,017,963 A | 1/2000 | Alfonso et al. |
| 6,029,663 A * | 2/2000 | Eisele et al. ........... 128/203.21 |
| 6,065,472 A * | 5/2000 | Anderson et al. ...... 128/203.21 |
| RE36,744 E | 6/2000 | Goldberg |
| 6,116,238 A * | 9/2000 | Jackson et al. ........ 128/203.15 |
| 6,193,985 B1 | 2/2001 | Sonne |
| 6,228,383 B1 | 5/2001 | Hansen |
| 6,234,366 B1 | 5/2001 | Fuchs |
| 6,255,502 B1 | 7/2001 | Penkler et al. |
| 6,274,635 B1 | 8/2001 | Travis |
| 6,397,838 B1 * | 6/2002 | Zimlich et al. ........ 128/200.14 |
| 6,608,073 B1 | 8/2003 | Hussain et al. |
| 6,610,271 B2 | 8/2003 | Wermeling |
| 2003/0077300 A1 | 4/2003 | Wermeling |
| 2003/0115133 A1 | 6/2003 | Wermeling |
| 2003/0163099 A1 | 8/2003 | Wermeling et al. |
| 2003/0206867 A1 | 11/2003 | Wermeling et al. |

* cited by examiner

Bias Spring Actuator Consisting of SMA Wire and Tension Spring

Bias Spring Actuator Consisting of SMA Wire and Compression Spring

PROGRAMMABLE MULTI-DOSE INTRANASAL DRUG DELIVERY DEVICE

This application claims the benefit of Provisional Application No. 60/225,624, filed Aug. 15, 2000.

FIELD OF THE INVENTION

The invention relates to a programmable intranasal drug delivery device for the controlled self-administration of a liquid pharmaceutical composition in the form of a spray or aerosol.

BACKGROUND

It has become acceptable medical practice to provide a patient suffering postoperative pain with means for self-administering an analgesic pharmaceutical composition. This practice allows a patient more direct participation and control over the pain management program and has been shown to have a beneficial psychological effect and can promote the overall recovery and rehabilitation of the patient.

It is also well known that the intranasal administration of a pharmaceutical composition in the form of a liquid spray or aerosol can elicit a much prompter physiological response than other routes, such as oral administration.

As presently employed, the self-administration of pain killers, which are typically categorized as controlled substances by the DEA, requires the patient to be provided with a permanent intravenous catheter to which is attached a tube that is attached to a container suspended above the patient for gravity feed of the analgesic. The tube passes through a bulky electro-mechanical device that can include a metering pump and that includes a microprocessor that will override the patient's demand for infusion of the drug if it exceeds a predetermined prescribed frequency or volumetric dosage. In other words, the patient is prevented from overdosing by a preprogrammed valve and/or pump that stops the flow of the liquid analgesic to the patient. In addition to being expensive, the existing programmable devices and systems for the self-administration of analgesics such as the opioids and other controlled substances are bully, require skilled personnel to set up at the patient's bedside, are expensive to maintain and occupy valuable space, not only in the patient's room but also in the health care facility's store rooms. These devices are also limited to the control of the administration of liquid pharmaceutical compositions via intravenous (and intra muscular) routes.

At least one opioid analgesic product has been approved by the FDA and is commercially available for nasal administration. The product is sold under the trademark STADOL®NS by Bristol Meyers Squibb of New York. The liquid pharmaceutical composition is contained in a screw cap bottle and is provided with a manually actuated pump for delivery of a spray into the nasal cavity. In addition to a priming procedure for the pump that is somewhat time-consuming and of potential difficulty for a post-operative patient suffering pain, the STADOL®NS system provides in excess of eight to twelve doses which could be self-administered in rapid succession by a patient that is not being supervised. This prior art device and system therefore requires the close supervision of hospital medical staff to assure that the patient does not overmedicate, and thereby self-administer a potentially lethal dose of the opioid. The container with the spray pump attached must also be removed from the patient's access in between doses. This procedure is time-consuming and burdensome for the medical personnel and is also potentially wasteful of the medication, since the system can only be used by one patient. A further drawback to this prior art system and its method of use is the known diversion and abuse that occurs as a result of the theft of the devices from the health care facility by workers.

It is therefore an object of this invention to provide a drug delivery device that will provide a plurality of predetermined doses of a pharmaceutical composition which can be used by a patient in need of treatment for the self-administration of one or more unit doses in accordance with a prescribed protocol that includes a time-delay between one or more prescribed unit doses.

It is a further object of the invention to provide a self-contained, compact and easily portable, programmable drug delivery device for the intranasal administration of a pharmaceutical composition that is safe, reliable and easy to use for self-administration by a patient in need of treatment.

Another object of the invention is to provide an intranasal drug delivery device which provides the administration of a precise volumetric unit dose of a controlled substance from a plurality of sealed containers in a system having access and control features that discourage diversion and abuse and that can deny use by unauthorized persons.

SUMMARY OF THE INVENTION

The above objects and other benefits and advantages are realized by the present invention of a programmable drug delivery device that is portable, i.e., hand-held, and manually actuated by the patient-user to sequentially self-administer a number of individual or unit-doses, e.g., 12 doses, from a plurality of separate sealed containers, where the interval between doses is predetermined and operatively controlled by electro-mechanical means that are integral with the delivery device.

The drug delivery method and apparatus of the invention provides multiple unit-doses of a drug for intranasal administration by the user. Access to a unit-dose of the drug by the patient-user is controlled by a program contained in an integrated circuit (IC) device or programmable microprocessor that is operatively connected to a mechanical or electro-mechanical locking means that automatically controls the advancement of the unit-dose containers. The microprocessor device is either provided with a program at the time of manufacture and/or assembly of the drug delivery device, or is programmable by a physician or pharmacist at the time that the drug delivery device is dispensed to the patient-user. The microprocessor includes a timer that controls the lock means that engages a magazine or other carrier containing a plurality of unit-dose containers. The sealed containers are arranged to move sequentially into a "ready" position that is aligned with the dispensing pump and manual actuator employed by the patient-user to release or discharge a pressurized dose via the delivery nozzle and ergonomic tip or cap into a naris and thereby into the nasal cavity.

The drug delivery device is completely integrated and self-contained in a portable hand-held housing of ergonomic design. The housing is secured at the time of assembly so that the individual drug containers cannot be removed without rendering the device inoperable. Tamper-evident features are also preferably incorporated into the structure of the delivery device. One or more long-life batteries, e.g., a battery having a shelf life of at least two years, can be installed at the time of manufacture and assembly, or the device can be provided with an accessible battery compartment for installation of one or more batteries when the delivery device is dispensed to the patient-user. Where the delivery device is programmed to provide a predetermined interval of time between use of the actuator to discharge the drug, an access port can be sealed or a program code interlock activated after the doctor or pharmacist has set the program control means. In one preferred embodiment, the programmed delivery interval is fixed at the time of manufacture and assembly of the drug delivery device of the invention and a seal or other mechanical blocking device is provided to prevent an inadvertent movement of the spray actuator. When the seal is removed in preparation for the first use, and the actuator is depressed for the initial use of the device, the battery circuit is completed and the microprocessor time clock is started.

In order to minimize the opportunity for improper diversion and use of the drug delivery device of the invention, a biometric or other personal patient identification means is incorporated into the device. Biometric identification means can include fingerprint identification means of the type that have been disclosed for use in connection with safety locks for handguns and other fire arms. Other personal identification means can include a series of numbers or other indicia that must be entered into an integrated push button or key pad that is operatively connected to the microprocessor and lock means. Such personalized patient-user identification requirements can be imposed either at the time of initial use, and/or for each sequential use. Unique encryption information is entered in each microprocessor at the time of assembly and the access code is printed on a label, an exterior sealing wrapper, or on other packaging material that is provided to the patient-user when the drug delivery device of the invention is dispensed.

The advantages of the drug delivery device of the invention will be apparent to those of ordinary skill in the art and include the following:

1. The opportunity and interest in diverting the nasal spray delivery device for recreational or other improper use of the drug by unauthorized individuals is minimized or eliminated.

2. The opportunity for abuse or misuse by patients who seek to self-administer the drug more frequently than is prescribed or safe is minimized or eliminated.

3. Patient compliance with the prescribed drug regimen can be improved.

4. An appropriate predetermined number of prescribed unit-doses up to the maximum capacity of the device can be programmed for delivery prior to, or at the time the device is dispensed to the patient-user.

5. More accurate and consistent doses are delivered by the device than can be achieved with the multi-spray pumps and reservoir systems of the prior art.

6. Each unit-dose of the drug is secured in its own sealed container.

7. The use of a hypodermic needle to inject the drug into a patient in need of treatment is eliminated.

The device of the invention also serves as a secure container for the storage of a plurality of vials containing controlled substances such as analgesic opioids in the form of liquid pharmaceutical compositions. Any action to remove the housing will result in disabling the pump, thereby denying access to any drug in the vials.

An audible or visible signal can be initiated in a preferred embodiment, for example, by having a blinking LED in the housing to alert the user that the device is available for administration of the second or subsequent dose.

In a preferred embodiment, the device is provided with a tamper-evident seal at the time of manufacture so that the prescribing pharmacist can insure that the contents are intact. The device is preferably constructed so that any effort at overcoming the delay mechanism will render the device inoperable by either causing a default in the microprocessor program, or by rendering the pump plunger inoperable, or both.

The invention is particularly advantageous in the administration of drugs where there are adverse side effects and health risks associated with overdoses. Since one type of drug to be administered in the class of pain killers can include narcotics, access to the drug must be limited by defining the period of time between doses, e.g., three-four hours. The microprocessor or other IC device is programmed to allow a vial to be aligned with the dispensing pump and in a position in which its contents can be administered after a physician or pharmacist has entered the prescribed interval.

Because each vial is sealed, its contents remain sterile during the storage period and even after the first use of the delivery device. Self-administration in a unit dose from each vial is initiated by a manual activation of a plunger which pressurizes the contents of a vial, while at the same time inserting one end of a delivery tube through a seal in the open end of the vial, thereby allowing the contents to be discharged through the tip of the nozzle and into the nasal passage.

The support member can be provided with a housing to enclose the vials and other operative mechanical elements of the delivery device. In one preferred embodiment, the exterior walls of the device are comprised of the housing and the outer side wall of the support member opposite the vials, and the two elements are rotatably engaged in a snap-fit and permanently sealed together to prevent access to the drug-containing vials.

In a second preferred embodiment, the support member is entirely encased in a pair of interlocking housing members which form the exterior of the device. In this second embodiment, the pump assembly is contained and supported by a pair of mating hollow pump support members projecting radially from the respective sides of the housing.

The elements forming the exterior of the assembled delivery device are preferred permanently joined so that access to the vials can only be obtained by breaking the assembly and thereby rendering it unusable and/or inoperable. The elements can be secured by adhesive, by ultrasonic welding of the plastic parts, by forming interlocking interior member in the respective parts that snap together, but that cannot be separated without damage, or by other means know in the art.

The force required to move the vial support member relative to the pump assembly can be provided by any motive means known to the art. The source of the motive force can include springs, such as coil springs or leaf springs, one or more elastic members extended between the moving elements, an electric motor, a manually applied force, and the like. In one preferred embodiment, a flat coil spring is secured at one end to the support member and at its other to the housing. A flat coil spring has the advantage of occupying minimal space in the housing. The coil spring can be wound into a tensioned state by rotating the housing and support member in opposite directions and then securing them by means of an escapement mechanism that permits partial rotation in the desired direction only upon release of the toggle member.

Motion can also be imparted by the use of an electric motor having a frictional member attached to one end of its drive shaft that makes direct contact with a driven surface of the opposing other member. A motor can also be utilized to rotate a gear wheel that directly or indirectly engages either a gear or toothed surface on the support member or the housing.

The motive force to produce relative movement can be provided by a mechanical linkage, e.g., a ratchet, that is engaged when the pump activator is depressed.

In another preferred embodiment, the housing is provided with an opening at its periphery which permits the patient's finger or thumb to contact the circumferential edge of the support member, thereby allowing the patient to apply a manual force to advance a vial containing the pharmaceutical composition into alignment with the pump assembly for dispensing the drug. The inclusion in this embodiment of a ratchet or other form of directional control means is particularly important to assure that an empty vial is not moved into the ready position. In this embodiment, the manual force is applied tangentially to an element at the periphery of the support member and generates a torque causing the support member to rotate about the central hub.

In the preferred embodiment where the plurality of drug-containing vials are arrayed radially on a generally circular support member, the device preferably also includes means for preventing relative movement between the pump assembly and the support member in a direction opposite to that which is intended. Means are provided for preventing a patient from rotating the housing to a position an empty vial in alignment with the pump assembly. Mechanisms for providing one-way rotational movement include a ratchet, where a separate pawl is attached to either the support member or the housing and flexes outwardly as the free end passes over a tooth or projecting element in the opposing portion of the assembly. The projecting teeth or similar features can be molded into the exterior surface of the central bearing hub of the support member and are provided with an angled cam surface on which the tip of the pawl rides as the support member advances relative to the pump assembly; each tooth ends in a square shoulder that engages a corresponding projecting surface at the tip of the pawl to put the arm of the pawl in tension when a force is applied to rotate the support member in the opposite direction.

Because of the relatively small incremental movements required to rotationally advance a vial from a fixed position to the ready position, the rotational bearing surfaces can be provided by adjacent cylindrical bearing walls that are integrally formed in the support member and in the single housing or the two-part housing elements.

The various elements comprising the support member and housing are preferably formed of molded polymer compositions. The polymer compositions are selected based upon having a relatively high resistance to impact fracturing, good resiliency in order to resist damage if dropped on a hard surface, and sufficient flexibility to facilitate the positioning of glass vials containing the pharmaceutical composition in the support member. The fabricated components are also to be made of materials that are sterilizable. The principal elements of the delivery device are preferably fabricated by injection molding. Suitable compositions included polyvinylchloride (PVC), polyethylene, acrylonitrile/butadiene/styrene (ABS), and the like.

As noted above, the drug delivery device of the present-invention includes an electronic control means that provides control of the dosage as well as control of the user interface to the device. In the preferred embodiment, the control means detects and records when a dose is administered, prevents the use of the device until the predetermined interval has elapsed following the previous use, provides feedback to the user and pharmacist or doctor as to the state of the device and accepts input from the user. In order to meet these requirements, the control means is advantageously embodied in an embedded microprocessor (microcontroller) capable of monitoring switches and sensors in the delivery device, interfacing with the user through input buttons and output devices, monitoring elapsed real time and actuating the electro-mechanical systems.

The electronic microprocessor control system provides the means for determining when user access to the drug to be administered shall be permitted and provides a user interface for the device. The microprocessor detects and records when a dose is administered, prevents use of the device until the prescribed time has elapsed, provides information to the user and attending health professionals as to the state of the device, and accepts input from the user and optionally, from the supervising health care professional who can enter the initial and/or changes to the protocol relating to the time lapse between doses. The microprocessor performs the functions of monitoring the condition of switches and sensors in the device, interfacing with the user through buttons and output devices, monitoring elapsed real-time and actuating the electro-mechanical systems which permit the drug to be administered.

The user interface can advantageously incorporate conventional push buttons for inputs and light emitting diodes (LEDs) or a liquid crystal display (LCD) to show the status of the system. Many different conventional interfaces between the input/output devices and the microprocessor are possible, with any desired degree of complexity. Accurate time bases can also be achieved with conventional techniques. Accordingly, the interface and timer structure will not be further described.

Actuation of the electro-mechanical portions of the delivery device in accordance with a prescribed time schedule is required in accordance with the present invention. As described above, a compact actuator for periodically toggling the escapement mechanism is necessary, given the overall size of the device. The actuator must be capable of pulling on the toggle mechanism with sufficient force to pull the link out of the recess in the bearing hub of the housing. Furthermore, the actuator is preferably compact and easily interfaced with the microprocessor. In a preferred embodiment, the escapement actuator is embodied in a wire with shape memory properties made out of nitinol. As is well known, the crystal structure of a nitinol wire changes when it is heated above a phase transition temperature, so that the wire is less stiff at cool temperatures than at high temperatures. Such a wire can therefore be used as an actuator by preloading the wire in tension.

BRIEF DESCRIPTION OF THE DRAWINGS

The above objects and other benefits and advantages of the invention will be apparent from the description which follows when read in conjunction with the attached figures in which.

DETAILED DESCRIPTION OF THE INVENTION

Figure 1:
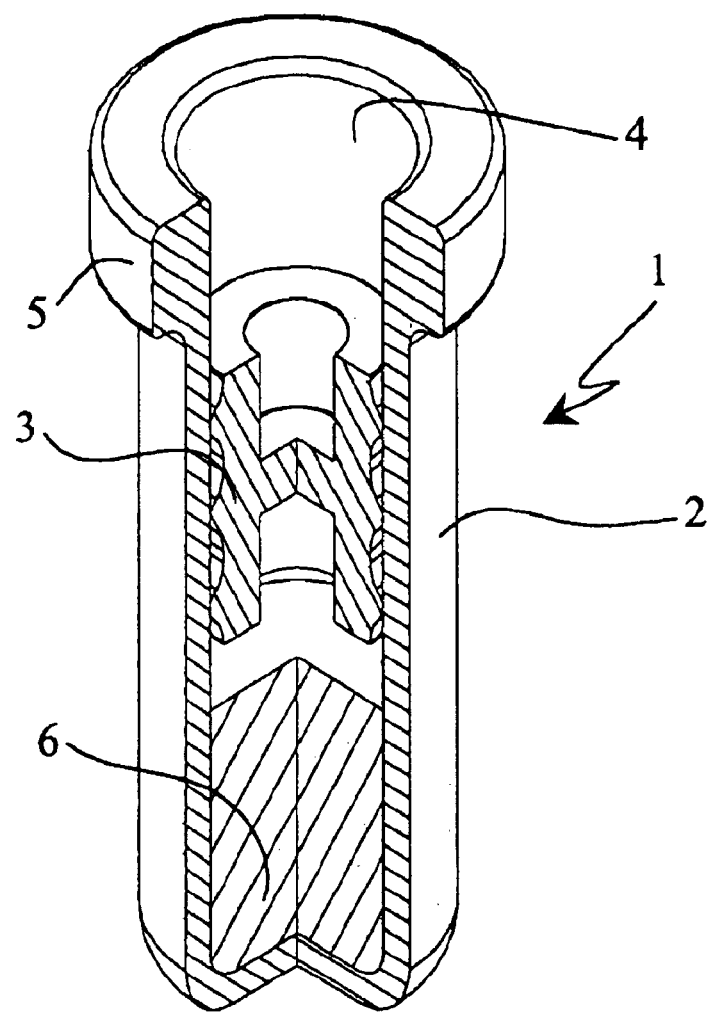
FIG. 1 is a perspective, quarter-sectioned schematic view of a precision drug dose storage vial containing a predetermined dosage volume of a liquid pharmaceutical composition.

Referring to FIG. 1 there is shown a sealed drug storage vial referred to generally as 1, comprising a generally cylindrical container 2 preferably formed of transparent glass that can be autoclaved for sterilization and sliding seal member 3 preferably fabricated from a heat and chemically resistant polymeric material that is slidably mounted in access orifice 4 of the vial. The vial contains a precisely premeasured dosage volume of pharmaceutical composition 1. In the embodiments described below, pharmaceutical composition 1 comprises a single or unit dose. However, as will be understood from the description that follows, each vial can be provided with a bi-dose volume which is intended for administration of a portion in each of the patient's nostrils utilizing a double-action pump assembly and actuator. In a preferred embodiment, the vial 1 is provided with a radially extending collar 5 to facilitate its handling during filling and assembly of the seal 3, and its positioning in the delivery device.

The discharge of the pharmaceutical composition 6 from the vial is described with reference to FIG. 2A where pump plunger 12 and piercing tube 14 are in contact with seal 3 and in communication with the interior of the vial.

Figure 2A:
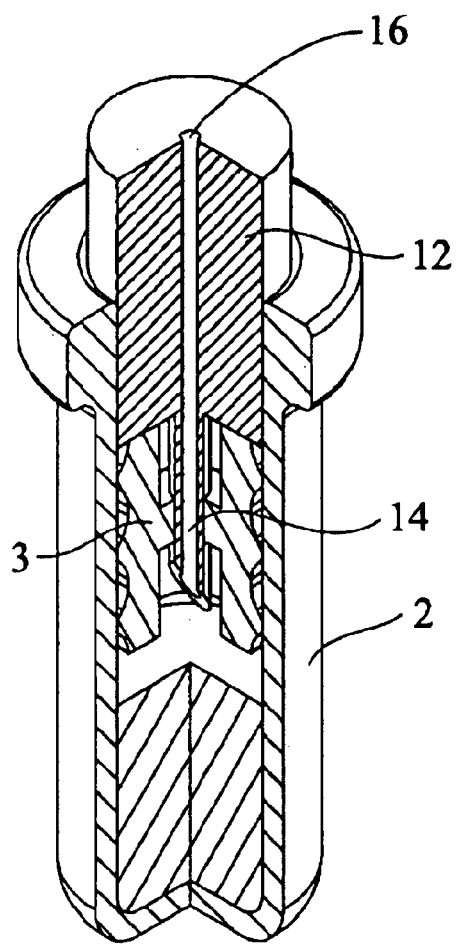
FIG. 2A is the drug storage vial of FIG. 1 into which has been inserted a piercing member and plunger that form part of the drug delivery channel at the initiation of the dispensing operation.
Figure 2B:
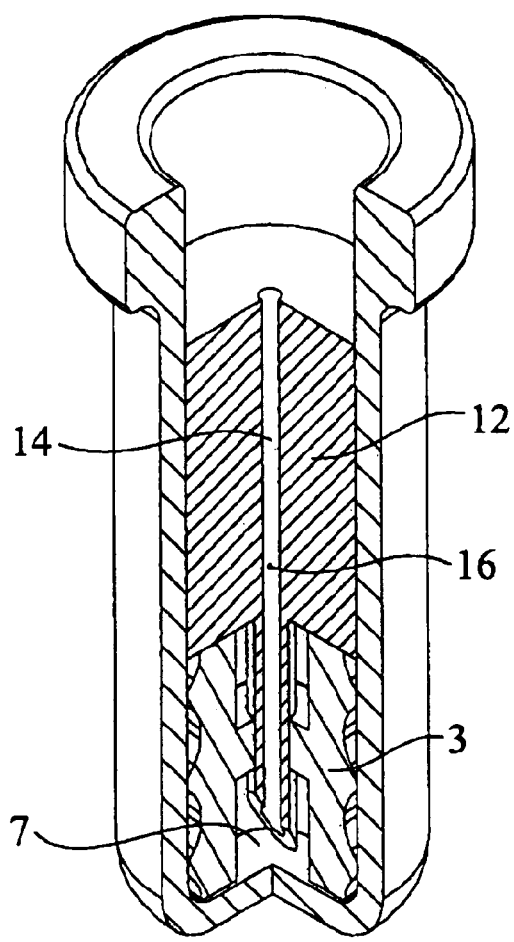
FIG. 2B is similar to FIG. 2A and shows the relative position of the elements at the end of the dispensing operation.

Referring now to FIG. 2B, the plunger 12 is shown in the fully extended position with the seal 3 advanced to the bottom of the vial. In accordance with the action of this positive displacement pump means, the liquid composition 6 has been expelled through the fluid channel 16 which extends coaxially through plunger 12 and tube 14. A recess 7 in the base of the seal provides an intake for piercing tube 14 which is all set sufficiently so that its sharpened tip is not dulled or bent by contact with the bottom of the glass vial.

Figure 3:
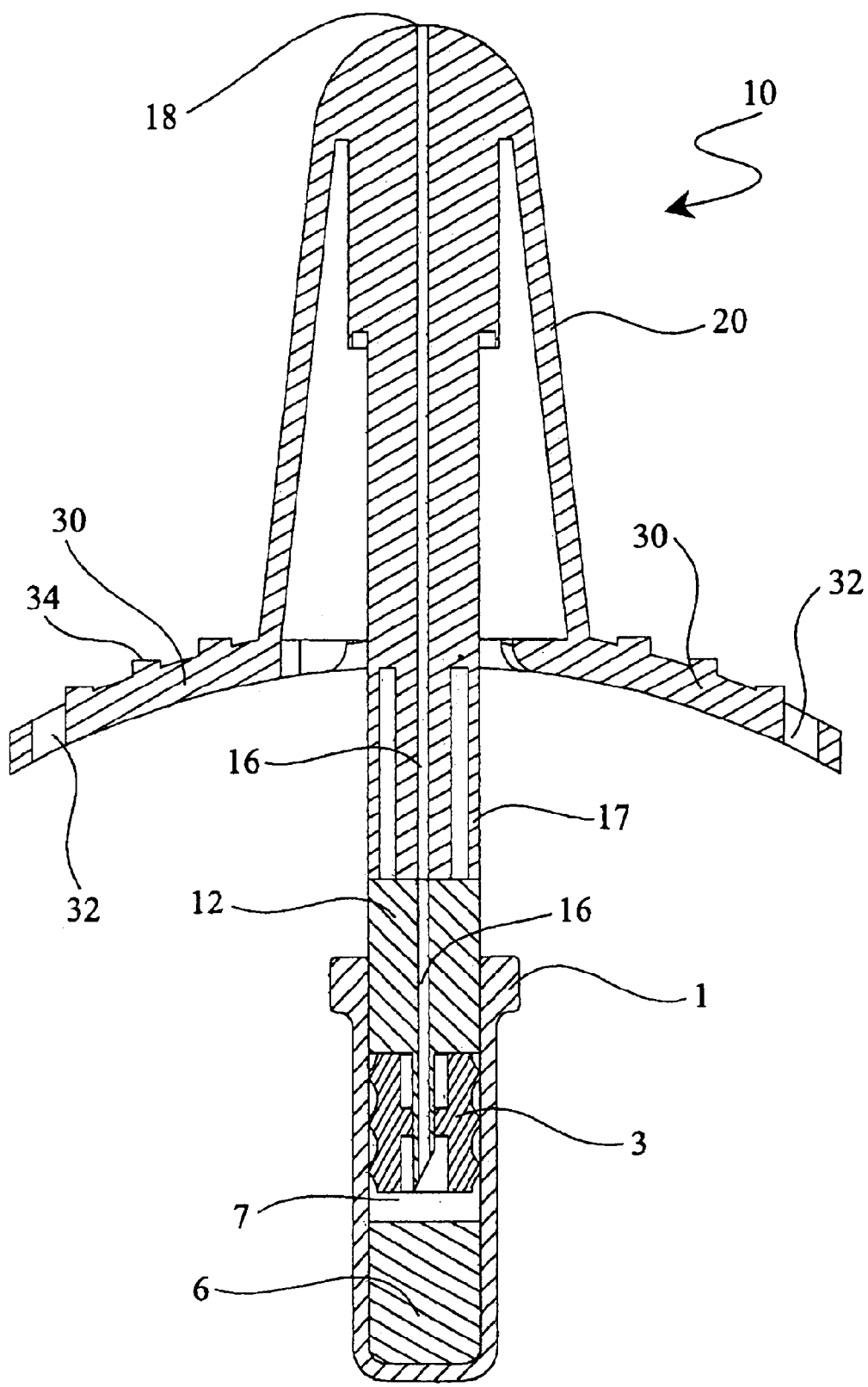
FIG. 3 is a side elevation view in section showing the nasal insert with flanking integral manual actuator flanges engaged in the ready position for dispensing with the apparatus shown in FIG. 2A.

With reference to FIG. 3, the pump assembly 10 is shown in cross-section with the plunger as positioned in FIG. 2A described above. As will be seen coaxially through pump supporting structure 20 and terminate at discharge port 18. As will be explained below, an ergonomic intranasal tip or nozzle is received on support 20. With continuing reference to FIG. 3, a pair of actuators 30 are provided with contoured surface elements 34 to receive the fingertips for manual activation of the delivery device. A locking orifice 32 is provided adjacent the free end of the actuator flange for cooperatively receiving a locking member of corresponding cross-section that is formed in the housing as described below.

The spray actuator assembly is comprised of components that are known in the art, for example, as employed in nasal spray devices manufactured by the Pfeiffer company, having offices in the United States and Germany.

Figure 4:
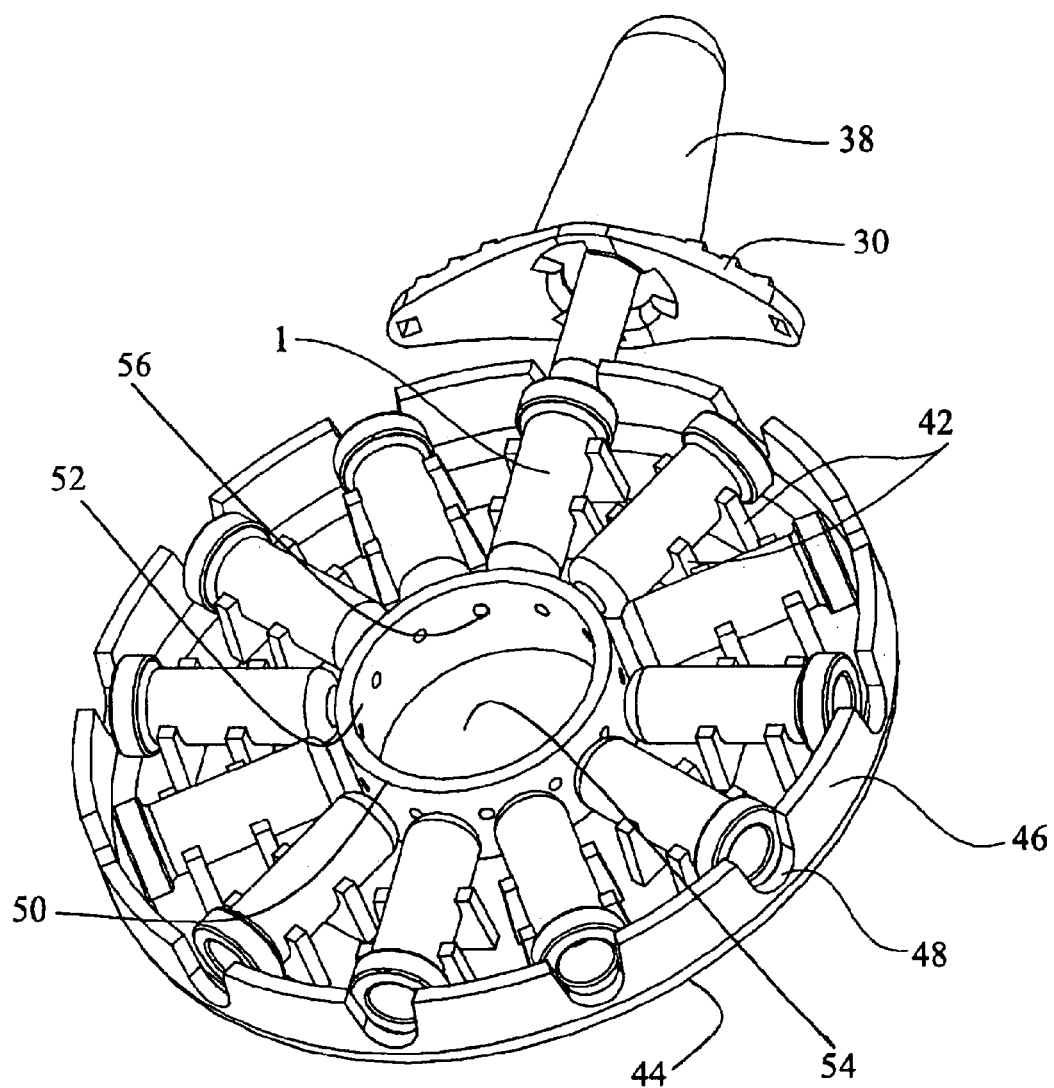
FIG. 4 is a top perspective view of one preferred embodiment of the invention showing a portion of an assembly in which a plurality of drug storage vials are arrayed radially in a circular supporting member for consecutive engagement by the nasal spray pump.

With reference to FIG. 4, the pump assembly and actuator with a vial is shown in a cooperative operating position with respect to support member 40 on which are securely mounted a total of 12 vials. In this embodiment, each vial is held in a snap-fit relation by a pair of generally U-shaped brackets that are integrally molded into the base plate 44 of support number 40. A peripheral side-wall 46 with a plurality of access ports 48 corresponding to the radially-positioned vials permits the pump assembly plunger to penetrate the access orifice when a vial is in the ready position. An annular wall 50 also rises vertically from the base plate 44 to form a central opening 54. Annular wall 50 is provided with a smooth bearing surface 52 for rotational engagement with a projecting wall of a housing element as will be described in more detail below. Annular wall 50 is also provided with a plurality of apertures 56 corresponding to the number of vials carried by the carousel-like supporting member 40.

Figure 5:
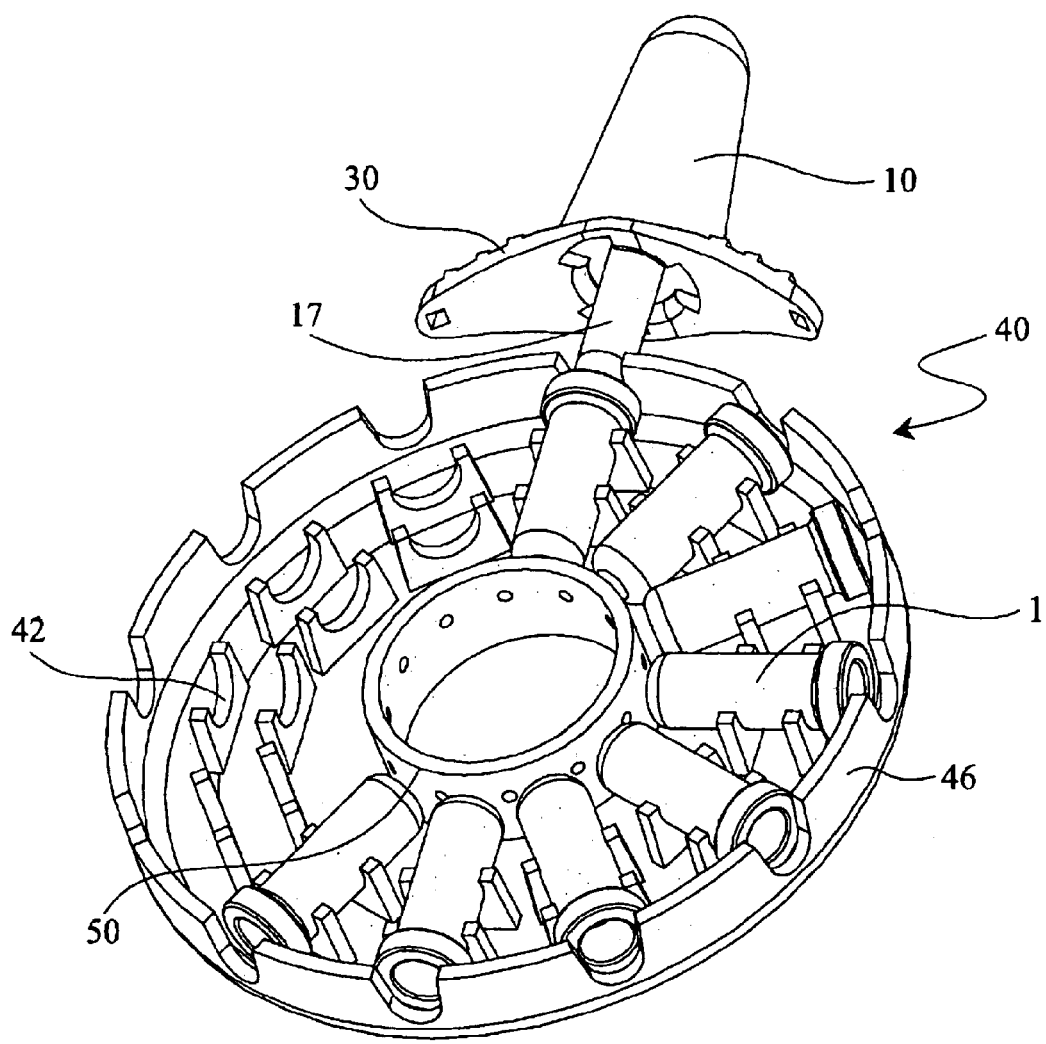
FIG. 5 is a view of a portion of the apparatus of FIG. 4 provided with less than its full capacity of vials.

It will be understood from the above description that the size of the supporting member is determined in part by the dimensions and number of vials to be carried thereon. For example, a lesser number of vials containing pharmaceutical composition can be loaded onto the twelve position supporting member as shown in FIG. 5, where the patient is prescribed to receive fewer doses, e.g. 8. However, as will be apparent to one of ordinary skill in the art, the diameter of the supporting member 40 could be reduced by changing the configuration of the sealed vials 1 e.g. by reducing their height and thereby the radial distance required between annular wall 50 and sidewall 46. Since ease of manufacture of the vial and installation of the seal and assembly of the sealed vial to the support member recommends a cylindrical configuration, the diameter of the vial would have to be increased to accommodate the same liquid dosage which is preferably in the range of 0.1 to about 0.2 ml. In the preferred embodiment described herein, the diameter of the assembled delivery device is preferably in the range of about three to five or six inches. This permits an ergonomic design that can be easily transported, stored in a pocket or purse and utilized by individuals of average strength and hand size.

Figure 6:
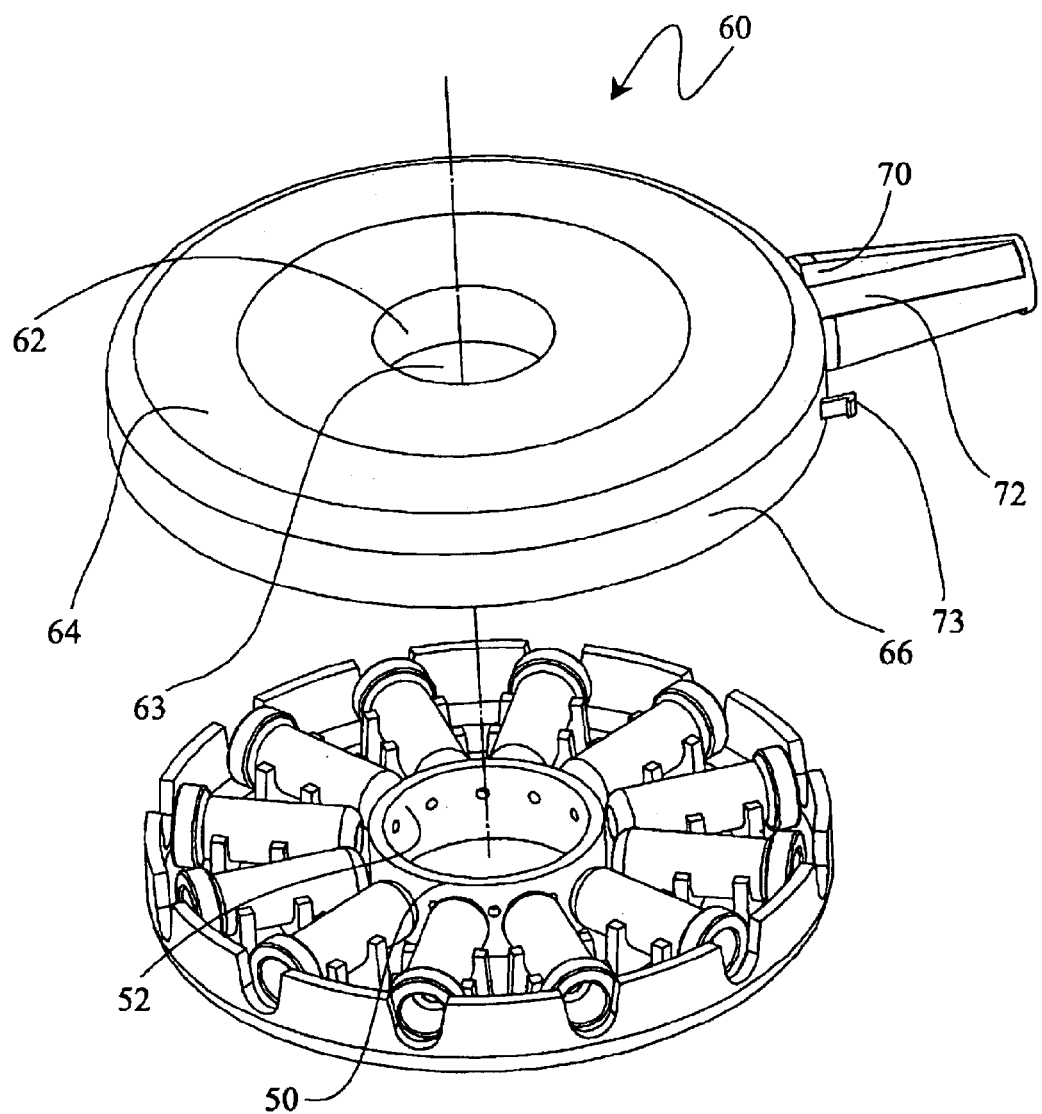
FIG. 6 is an exploded perspective view illustrating the assembly of a support member containing vials similar to that shown in FIG. 4 and an associated housing.

With reference to FIG. 6, the support plate is shown in position ready for assembly with housing 60 that is received in a close-fitting, rotatable relation. Housing 60 includes a central annular wall 62 having on its interior a depending bearing surface 64 shown in FIG. 15 that is received in sliding contact with the bearing surface 52 of annular wall 50. Wall 64 extends outwardly from annular wall 62 and terminates in downwardly depending side-skirt 64. Pump support 70 is integrally molded and extends radially from side-skirt 66, and is provided with pump bearing channels 72 for receiving a pump assembly 10 in sliding relation. A coil spring 80 is received cooperatively on pump support 70 and engages the interior of pump assembly 10 to provide a biasing force extending outward radially so that pump plunger 12 and piercing tube 14 are retracted to the interior of pump support 70 during rotation of the support member 40 relative to housing 60.

Figure 7:
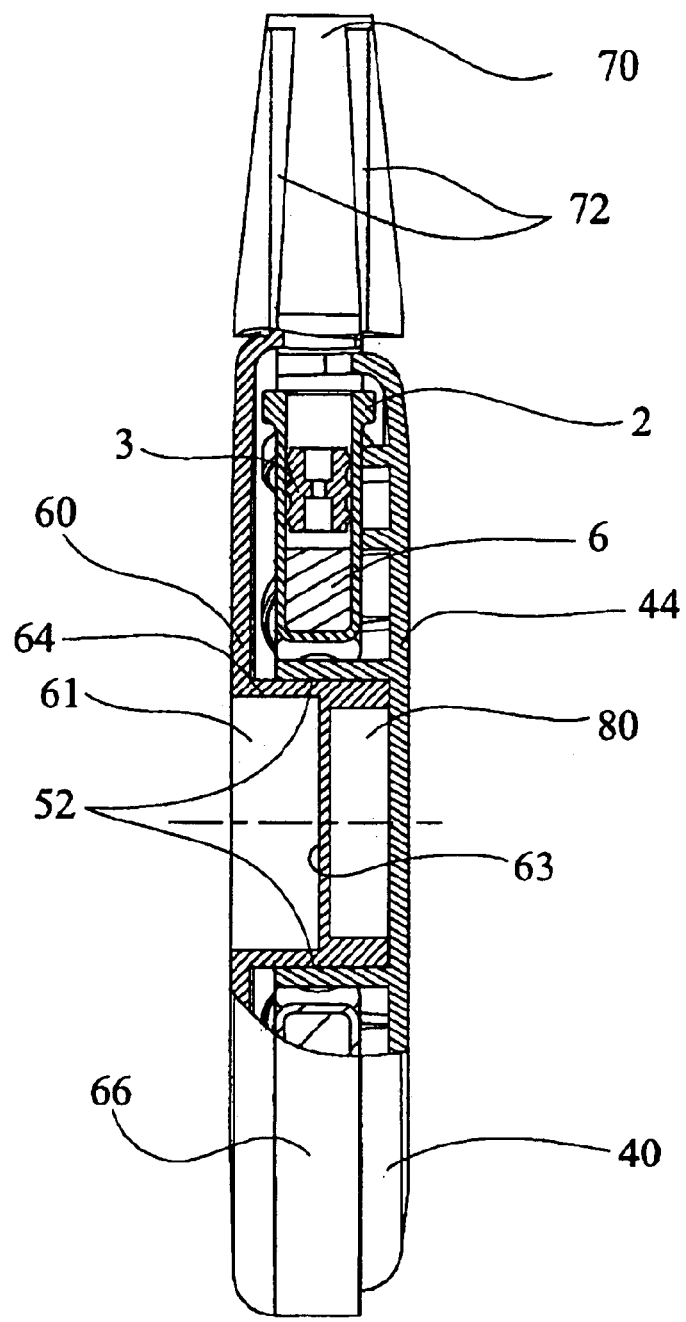
FIG. 7 is an end elevation view, shown partly in section, of the assembly of FIG. 6.

In the partially sectioned view of FIG. 7, housing 60 is assembled to support member 40 thereby forming an enclosed compartment 80 bounded by the floor 63 of open chamber 61 of the housing 60.

Figure 8:
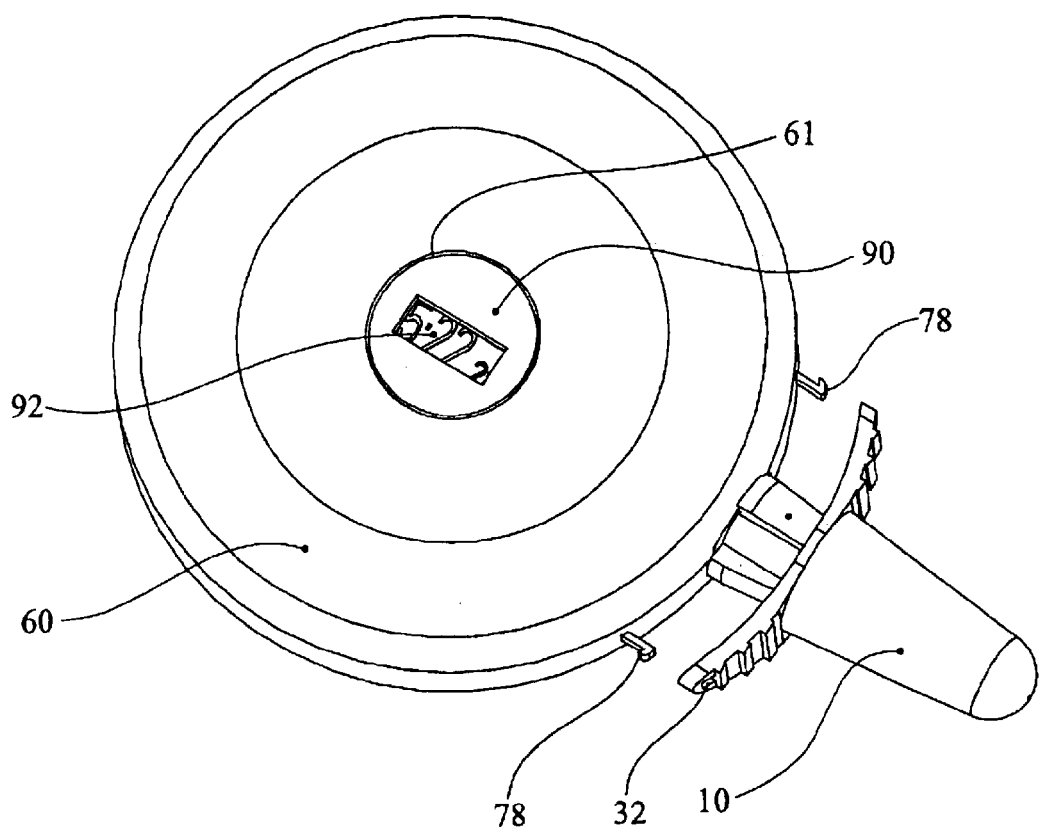
FIG. 8 is a perspective view showing the assembly of FIG. 6 that also includes a nose cap and an electronic control module with a visual display.

As shown in FIG. 8, electronic module 90, preferably including a display 92 for providing status information to the patient or health care supervisor is received in chamber 61 of housing 60 the electronic display can provide information such as the number of doses remaining in the delivery device, the time remaining until the next dose can be accessed, encoded patient identification information, delivery device, serial number, battery life, and the like. In a further preferred embodiment, the electronic module can include one or more input/activation switches in the form of push buttons or touch-sensitive devices. The switches then control functions such as audible/visual alarms or signals, initial battery activation/power activation, entry of prescribed delay time between doses, and the like.

The electronic interface module 90 can also include means for uniquely identifying the designated patient/user of the delivery device utilizing state of the art technology. For example, an electronic interlock can be provided that is activated only when the authorized user's fingerprint is read prior to actuation of the pump assembly to discharge the pharmaceutical composition. The required recognition program can be incorporated into the microprocessor or included as an auxiliary device that performs as a yes/no switch or function in the release of the mechanism to move a vial into the ready position for actuation.

Figure 9:
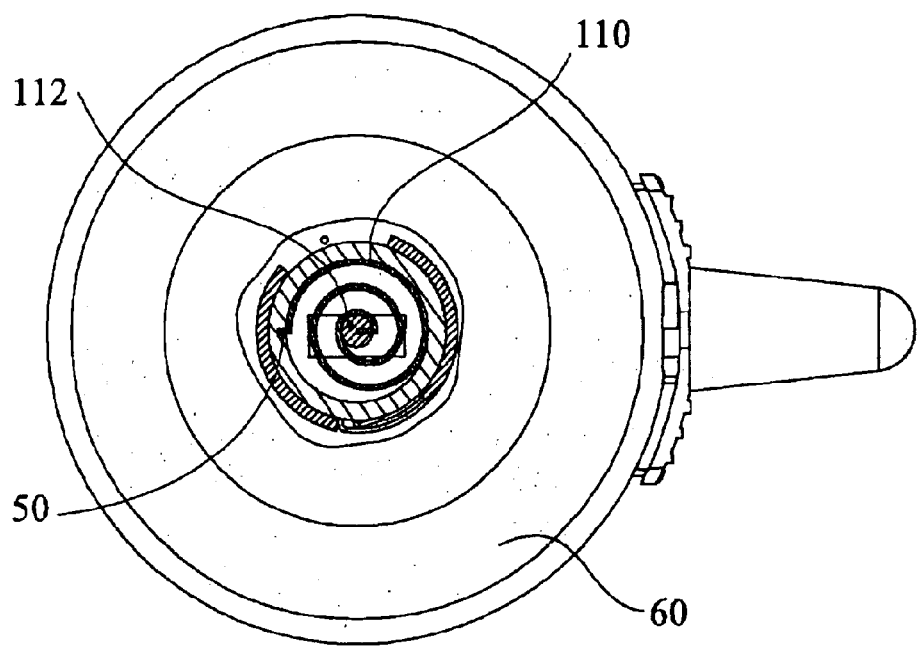
FIG. 9 is a side top view, partial cut away, showing the complete assembly of FIG. 8 with the pump assembly and nose cap in the locked position and schematically illustrating one embodiment of a centrally-positioned coiled power spring.

As noted above, a coil spring such as that illustrated in FIG. 9 is a preferred source of the motive force required to provide relative rotation between the pump assembly and the vials secured to the support member. In the embodiment shown, one end of flat coil spring 110 is secured to a post that is integrally formed in the center of the housing 60. The opposite end of the coil spring is secured to annular wall 50 of the support member 40. As will be understood by one of ordinary skill in the art, the arrangement of post and attachment point can be reversed, and a variety of other mechanical constructions can be adopted to provide the motive force. For example, an extensible elastic member can be attached at one end to the sidewall 46 of supporting member 40 and stretched about its periphery in a channel provided for that purpose for attachment to the interior of housing side-skirt 66. The elements are assembled with the elastic member in a relaxed state and counter-rotated one or more full turns in order to provide sufficient torsional force in the extended elastic member to produce relative rotation through at least one revolution to bring each of the radially positioned vials into a ready position.

Figure 10:
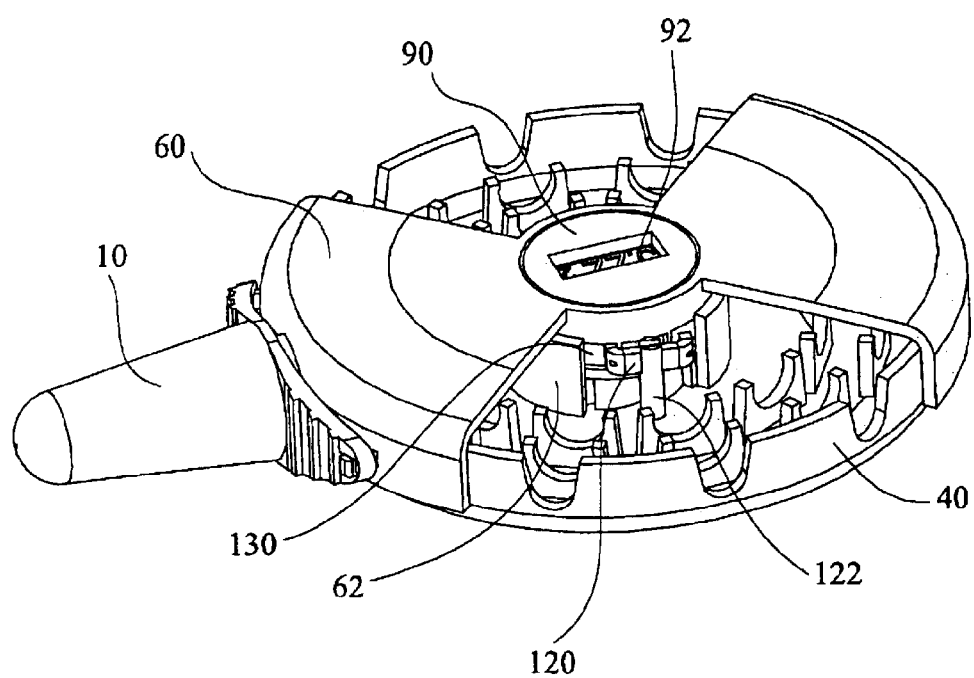
FIG. 10 is a perspective view of the assembly with the housing partially cut away and the vials removed for clarity to illustrate an escapement mechanism for controlling the movement of the vials with respect to the pump.

In a preferred embodiment, and as best shown in FIGS. 8 and 10, a lock mechanism is provided for securing the pump assembly 10 in the fully inserted position and with pump actuator flanges in contact with the periphery of housing 60. This can be accomplished by providing one or more lock elements 18 that releasably engage the actuator after passing through lock securing apertures 32. This provides a compact and secure configuration for the delivery device that minimizes risk of damage if the device is being carried in the user's pocket or handbag.

In order to avoid the undesired inter-locking of the pump assembly after the first use, as in an institutional setting, the projecting lock elements 78 can simply be snapped off in preparation for use of the delivery device by the patient.

It will also be understood that the drug delivery device can be shipped after manufacture with the pump assembly depressed and locked into an empty vial, e.g. after a quality control test to confirm the spray function; or by omitting a vial from one position. This procedure would provide one less dose than would otherwise be available for patient self-administration.

If the pump assembly is to be shipped in the fully extended position, a removable restraining clip (not shown) or split collar can be inserted below the actuator flange 30 and between the housing 60 to prevent the inadvertent discharge of the drug. The retaining clip can also be reinstalled between uses for the same purpose.

Figure 12:
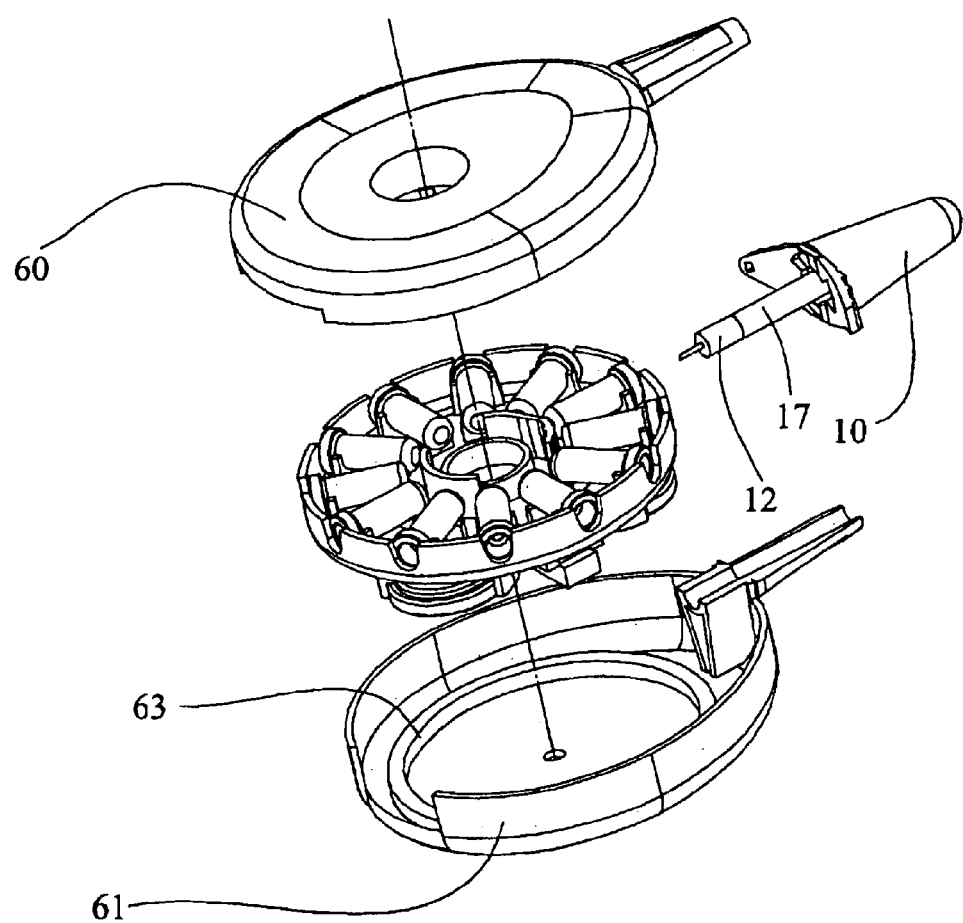
FIG. 12 is an exploded perspective view of another preferred embodiment in which a two-part housing encloses the support member.

In a further preferred embodiment illustrated in FIG. 12, a two-part housing consisting of elements 60 and 61 completely encloses the support member 40 in a secured, mated relationship. In this embodiment, the pump support is also formed in two mating half-sections having an interior pump bearing channel for receiving the plunger 12 and extended tubular member 17. The lower housing section 61 is provided with an upstanding internal annular rim which further supports and encloses the components positioned on the underside of support member 40. In this regard, reference is made to FIG. 15 in which the electronic components, including a plurality of batteries 260 retained by battery supporting members 262 are securely positioned adjacent the microprocessor 270 that is mounted on supports 272. A plurality of apertures 276 are provided for the passage of wires from the opposite side of base plate 44.

Figure 14:
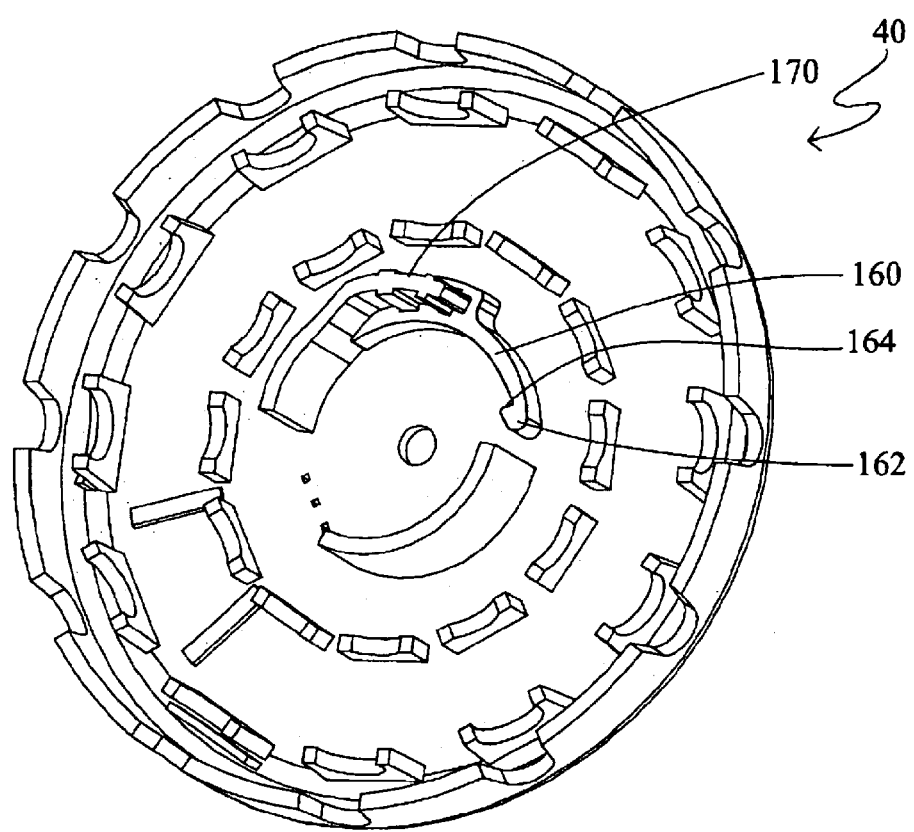
FIG. 14 is a perspective view of a support member illustrating the placement of a ratchet arm.
Figure 15:
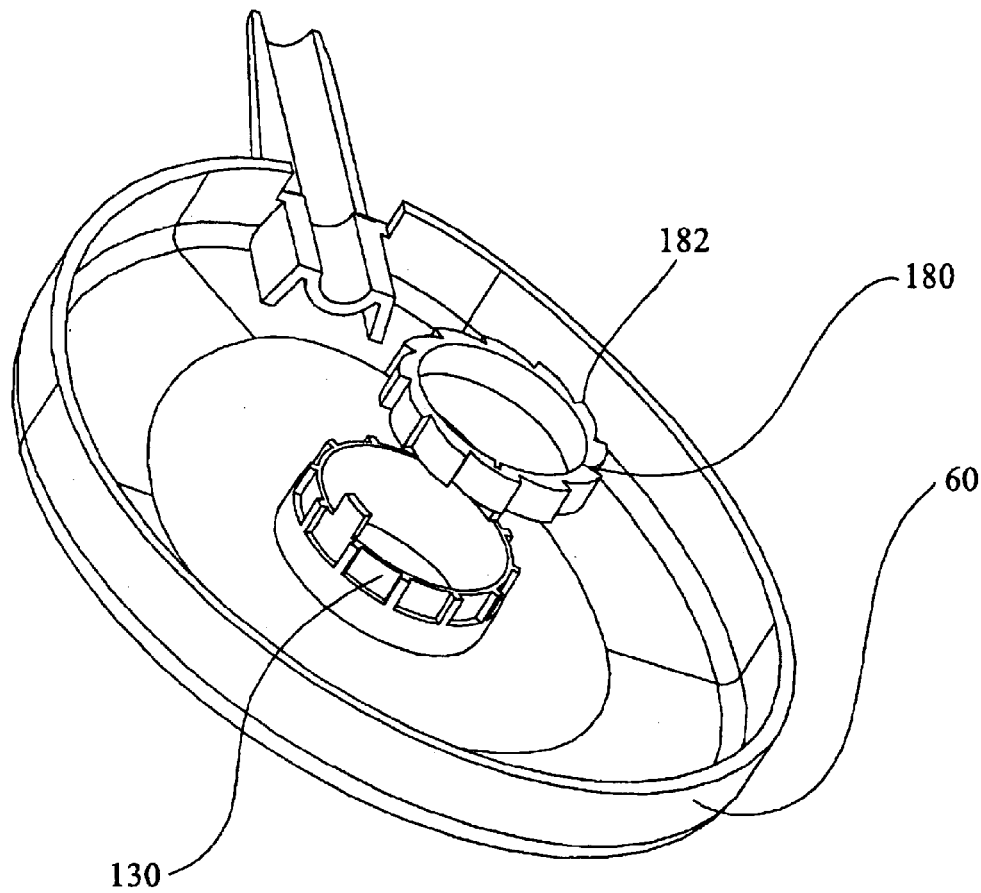
FIG. 15 is a perspective view of the interior of one side of a two-part housing illustrating the assembly of an annular ratchet wheel with external teeth intended for engagement with the arm shown in FIG. 14.
Figure 16:
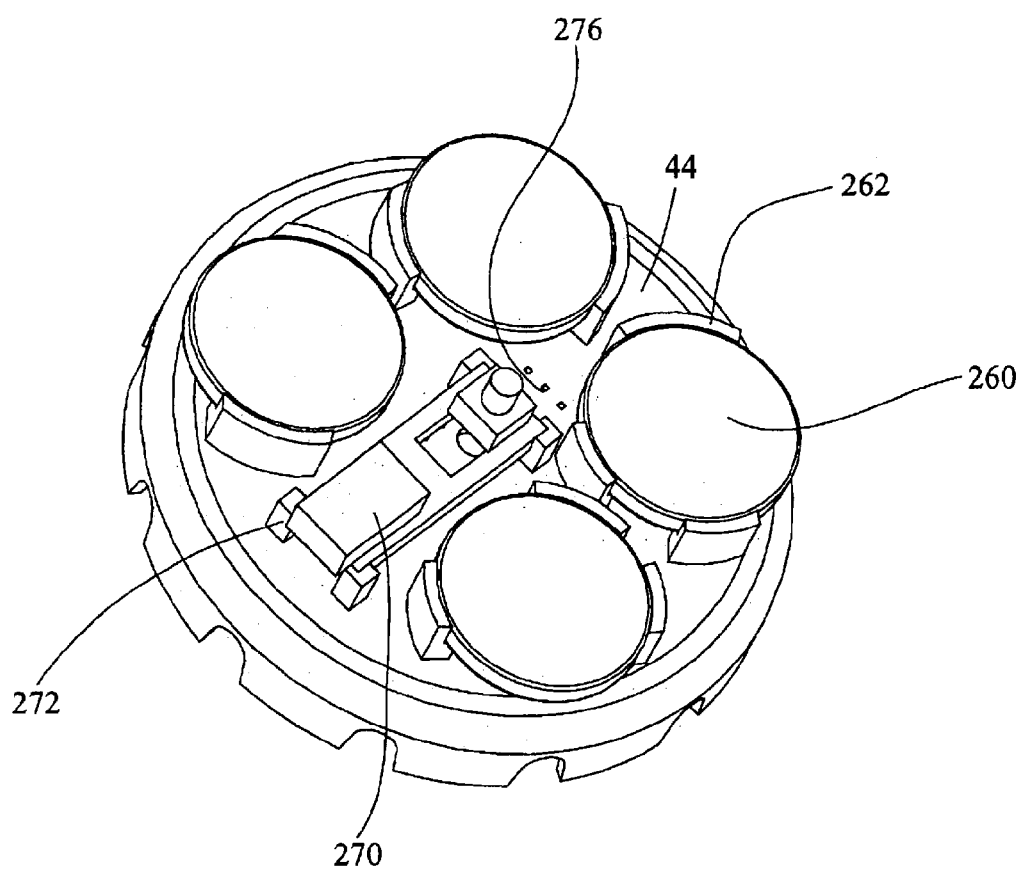
FIG. 16 is a view of one embodiment of a support member illustrating placement of batteries and other electrical components.

In order to provide an added measure of safety and security by insuring that the relative motion of the support member and pump assembly cannot be reversed, a ratchet such as that illustrated in FIGS. 14 and 15 is provided. Shown in FIG. 14, ratchet arm member 160 is mounted on supporting wall 170 by a sliding engagement which secures one end of the arm in a fixed position. The pawl tip 162 surface 164 would engage a correspondingly configured groove 182 that is formed in the separate ratchet wheel 180. As further shown in FIG. 15 ratchet wheel 180 is received in a secure engaged position on annular wall 62 of housing 60 secured there as by adhesive or mechanical fasteners.

Figure 13:
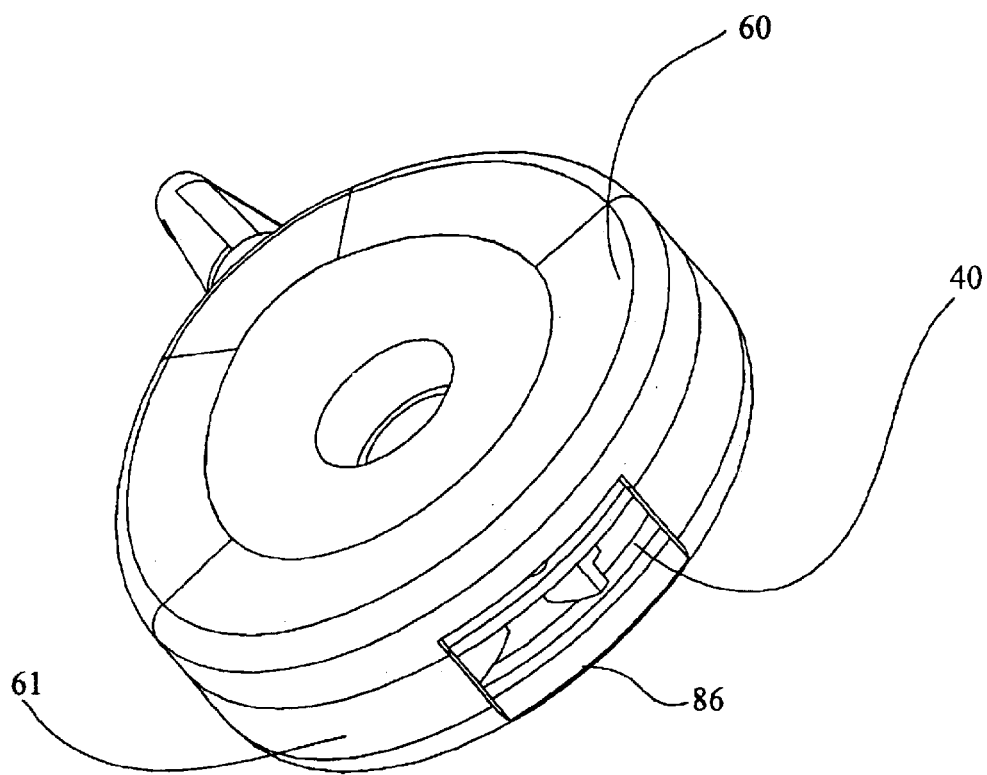
FIG. 13 is a perspective view of the assembled delivery device similar to FIG. 12, but illustrating an embodiment in which the housing is provided with a window aperture to access the interior.

The use of a ratchet or other means to preclude reversing the direction of relative movement is particularly important where the motive force is manually applied by the patient, as for example, in the embodiment illustrated by FIG. 13. In this embodiment, a two-part housing is provided with an access window 86 of sufficient dimensions to permit the insertion of a finger or thumb to rotate support member 40 that is mounted inside the housing elements 60, 61. In this embodiment, where a manual motive force is to be applied, the microprocessor can cause an audible and/or visual signal to be emitted which alerts the user to a status in which the escapement has been actuated to permit movement of the support member to position a vial in the ready position.

Figure 11:
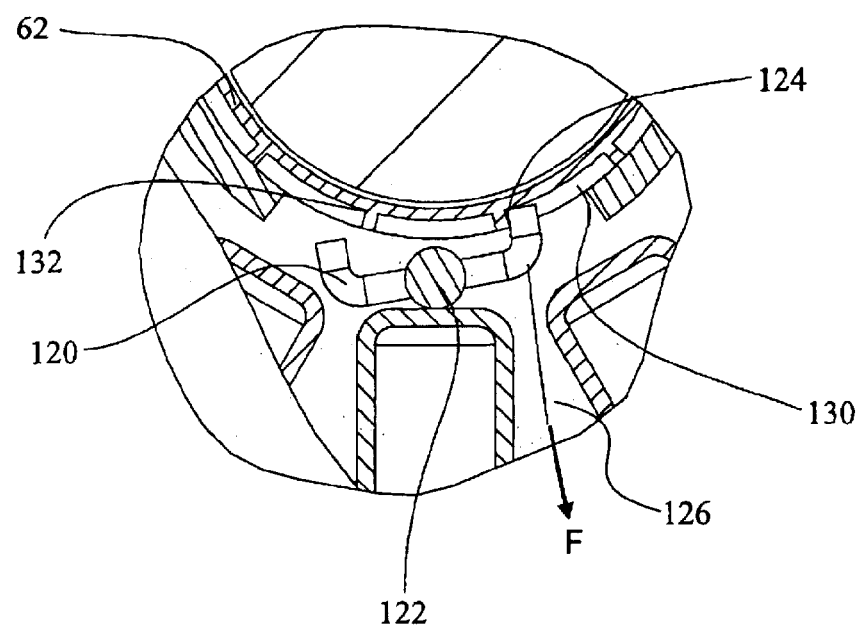
FIG. 11 is an enlarged detail, shown partly in section, of a plan view of the escapement mechanism and activator wire.

In order to insure the patient's safety as determined by the prescribed protocol, the drug delivery device of the invention is provided with means for controlling the movement of a vial to the ready position following the required time delay after the composition was last administered. In one preferred embodiment, an electro-mechanical interlock is provided utilizing an escapement mechanism such as that illustrated in FIGS. 10 and 11. A generally U-shaped control arm 120 is pivotally mounted on pivot post 122 supported on base plate 44 of support member 40. As best shown in FIG. 11 the tip 124 of control arm 120 extends in to a recess 130 formed by projecting stops 132 extending outwardly from annular wall 62 of the housing 60. Escapement actuating means 126 is shown schematically as applying a force F to one of the control arms to cause a pivoting or toggle motion. As will be understood by one of ordinary skill in the art, the size and spacing of the distance between the control arm tips 124 corresponds to the distance between projecting stop elements 132, so that as the control arm 120 is pivoted to allow relative movement between the housing and support member, the opposite end of the arm 120 enters the adjacent recess 130 and its tip 124 engages the next stop thereby 132 allowing the controlled and limited movement of an adjacent vial into the ready position.

The force F can be provided by any of a variety of electro-mechanical devices including a single- or double-acting solenoid which is capable of pushing and pulling a connecting rod either directly, or through a series of levers attached to the control arm 120; an electric motor to which is attached a cam or cammed lever, where one or more solenoids or the motor are caused to operate by signals received from the microprocessor.

In a particularly preferred embodiment, shape memory alloy (SMA) wire is employed in conjunction with an escapement mechanism for advancing the support member relative to the pump assembly. Two methods that are well known for creating linear actuation using shape memory alloy will be described with reference to illustrative schematic diagrams. Both methods are referred to as bias spring actuators, since the SMA wire is pre-loaded using springs. The two constructions differ in that one utilizes a tension spring and the other utilizes a compression spring. Either method can be utilized in the present invention and their application in different embodiments is illustrated and described in conjunction with FIGS. 22A and 22B.

Figure 22A:
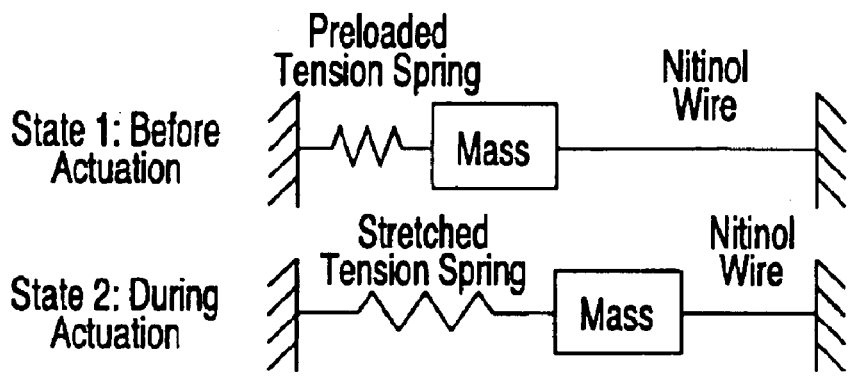
FIGS. 22A and 22B are schematic illustrations of extension and compression bias spring actuator systems.

FIG. 22A illustrates the principle of a bias spring actuator employing a spring in tension. A mass M is connected to a tension spring on one side and a nitinol SMA wire on the opposite side. The tension spring is stretched so that a preload force exists in the spring and SMA wire. The wire contracts when the shape memory effect is initiated by heating the wire to a temperature above its phase transition temperature. When the wire contracts it pulls against the tension spring and causes the mass to move. When the SMA wire cools and returns to a temperature below its phase transition temperature, the SMA wire elongates. The tension provided by the spring is necessary for stretching the SMA wire back to its original length.

Figure 22B:
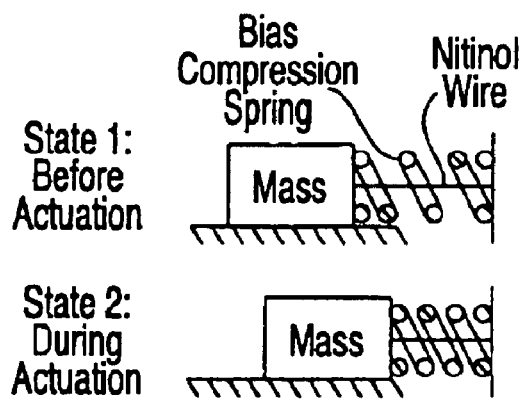

In the second type of bias spring actuator, a compression spring replaces the tension spring. This construction is illustrated in FIG. 22B where a compression spring pushes against a mass M, and the shape memory alloy wire pulls on the mass. In the construction of the invention, it is preferable that the wire pull through the center of the spring, as shown. When the SMA wire is heated and shortens in length, the compression spring is further compressed. As the SMA wire cools, the compression spring pushes against the mass M and stretches the SMA wire back to its original length.

The bias spring actuator provides an electro-mechanical device in which the intermittent application of an electric current to a length of nitinol wire attached to an element M, such as one end of a pivoting escapement that is bias-positioned by a spring, arm will cause the arm to move and thereby permit the rotating member to advance to the next permitted position.

In another preferred embodiment which will be described with reference to FIGS. 17, 18 and 19, the pivotally-mounted escapement control arm 120 is actuated by a force resulting indirectly from the passage of an electrical current through a length of nitinol wire 200 or other shape memory alloy (SMA) wire. With reference to a first embodiment illustrated by FIG. 17, a length of nitinol wire 200 is slidably retained in a channel 202 formed by a pair of, adjacent walls 204, the free end of wire 200 being fixed to a conductor element 210 which extends below the base plate 44 of support member 40 for a connection to a power source through appropriate circuitry described below.

The opposite end of SMA wire 200 is joined by connector 220 to a length of flexible braided steel wire 230 preferably having a diameter of about 0.0006 inches, which wire passes freely through a thin-walled plastic tube 226 held by bearing blocks 228. Wire 230 also passes through slide elements 240 that contact opposite arms of control arm 120. The free end of the steel wire 230 is joined through a connector 220 to tension spring 232 which in turn is secured to anchor post 234 that is affixed to base plate 44. It will be understood that SMA wire 200 forms part of an electrical circuit such as that described in the schematic of FIG. 20 which includes a capacitor whose charge can be passed through and thereby raise the temperature of the SMA wire to a point at which it physically contracts to reduce its length by up to 4%. As SMA wire 220 contracts, it pulls steel wire 230 which in turn causes a force to be applied to pivot arm 120 via slide elements 240 to which it is secured. As explained above, the application of this force F through steel wire 230 allows the relative movement of the housing and support member and the positioning of a fresh vial in the ready position.

Figure 17:
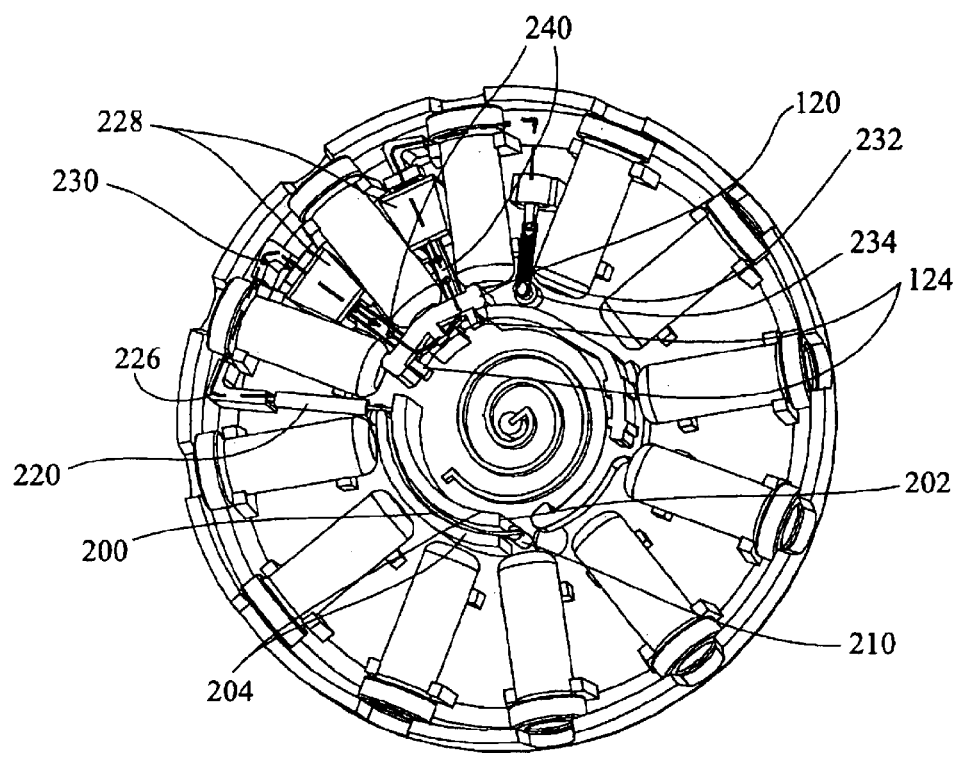
FIG. 17 is a top plan view showing a first embodiment of an electro-mechanical actuator for a release mechanism.
Figure 18:
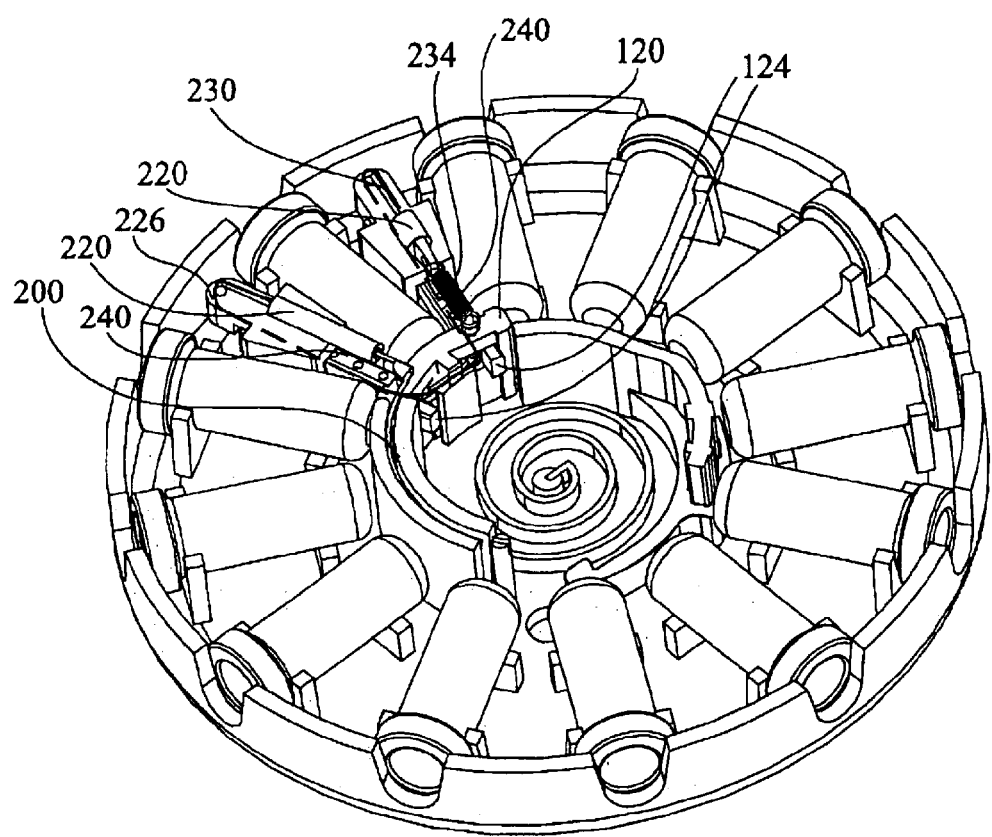
FIG. 18 is a view similar to FIG. 17 showing a second embodiment of the mechanism.

In a second preferred embodiment for the application of an actuating force to the escapement control arm 120, reference is made to FIG. 18 where like reference numbers are used to identify the elements described in detail in FIG. 17. In this second embodiment, the length of the nitinol SMA wire 200 is increased and the steel wire 230 is channeled through tubes to form a pair of vertical loops; however, the method of operation is otherwise the same.

Figure 19:
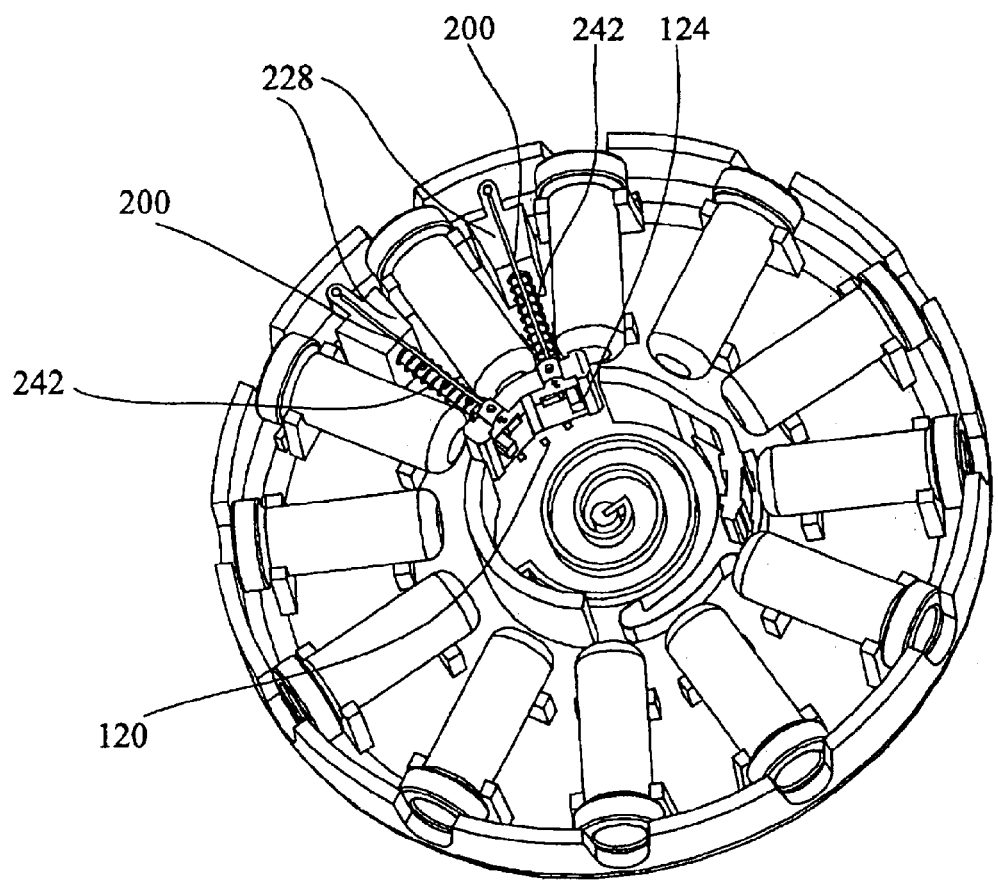
FIG. 19 is another view similar of FIG. 17 showing a third embodiment of a release mechanism.

In the third and most preferred embodiment that is illustrated in FIG. 19, two separate SMA wires 200 are employed and each is preloaded by a compression spring 242, as compared to the use of a single tension spring 232 as was described in the prior two embodiments. In order to actuate the escapement by application of the force F, current is passed through the SMA wire 200 attached to the tip of the control arm 120 that is in restraining contact with projecting stop 132, thereby withdrawing the tip 124 and allowing relative movement of the housing and support member, while at the same time positioning the opposite end of the control arm 120 in a position to engage the next projecting stop 132. It will be understood that additional circuitry is required to connect one end of each of the two SMA wires to the capacitor through a switch that alternately delivers the current to the wire that is engaged with the escapement in accordance with the time delay protocol prescribed by the microprocessor.

In accordance with the present invention, the microprocessor controls the nitinol wire actuator so that a dose can be given only at the predetermined and prescribed time intervals. This means that the microprocessor must supply the actuator with sufficient power at the predetermined time intervals so that the actuator can pull the escapement to permit the motive force applied to the support member to advance the vial, but at all other times the microprocessor does not supply the actuator with power, which prevents the administration of a dose during the time intervals.

Actuation of a nitinol wire requires a significant amount of power. One of the primary requirements of the electronics design therefore is to apply sufficient power to the nitinol actuator from the limited voltage and current available in a small button cell battery compatible with the space restraints for the device of the present invention.

In a preferred embodiment, it has been determined that the diameter of the nitinol wire should be 0.0006 in./0.15 mm and the displacement for each actuation 4.0 mm, which means that 100 mm of wire is required in total. The 0.15 mm wire has a characteristic resistance of 4.3 ohms/cm, yielding a total resistance of about 4 ohms. For nitinol wire with a 0.15 mm diameter, it is preferred that 200 mA be applied to the wire for one second in order to actuate the wire.

The peak current generally available from a conventional 3V button cell battery that meets the volume constraints of the device of the present invention is on the order of 150 mA. Therefore, in accordance with the present invention, an energy store has been designed using a capacitor that can be slowly charged over a matter of minutes from the battery and discharged into the nitinol wire for one second at a high current level.

Moreover, to enable computer control of the operation of the device, the charging of the capacitor and the energizing of the nitinol wire from the capacitor must be done under microprocessor control. While processors such as the known commercial PIC12C924, and others, can support an LCD display, a simple user interface and programming scheme can be implemented with a much smaller and simpler microcontroller. The commercially available PIC12C5XX processor is suitable for controlling the device via one of a preselected dispensing schedules.

This type of microprocessor can control the charging/discharging circuit for the capacitor, the position sensors in the device and any buttons and LEDs in the user interface. The logic levels available on its CMOS outputs running on a 3V button cell battery are 2.3V at 25 mA (100 mA with GPIO parts) for the logic one output, and 0.6V at 25 mA (100 mA with GPIO parts) for the logic zero output. These voltage levels can be used to switch transistor circuits to charge the capacitor.

Figure 20:
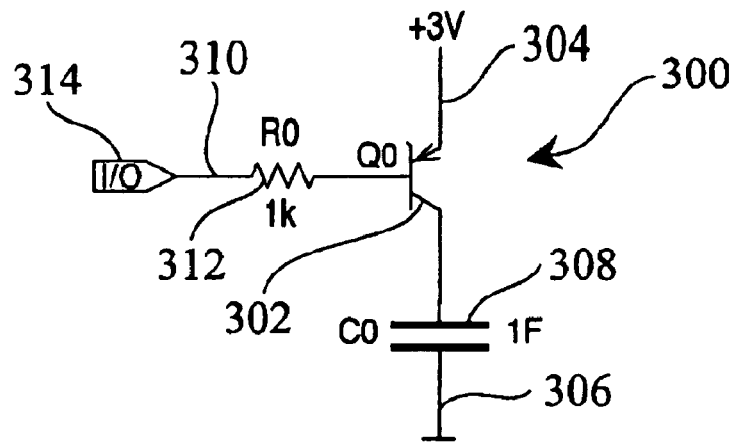
FIG. 20 is a schematic diagram of a preferred embodiment of a discharge circuit used to activate an element in the assembly.
Figure 21:
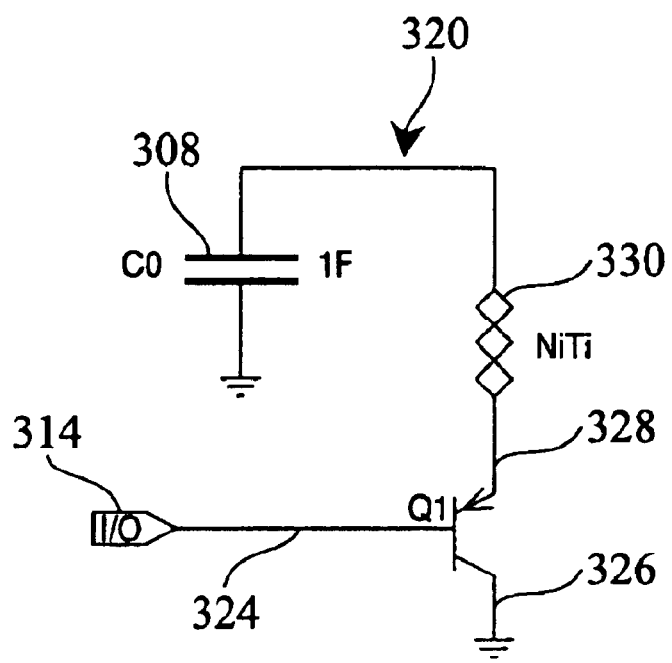
FIG. 21 is a schematic diagram of a preferred embodiment of a charging/discharging circuit used in the assembly.

FIG. 20 illustrates a basic capacitor circuit 300 usable in accordance with the present invention. As shown therein, the capacitor circuit 300 includes a bipolar inverted transistor Q0 302 having an emitter 304 connected to the nominal 3V of the battery and a collector 306 connected through a 1 F capacitor C0 108 to ground. The base 310 of transistor Q0 is connected through a 1 k ohm resistor R0 312 to an input/output 314, e.g. a push button to initiate delivery of a dose. In accordance with well known principles, a charge can accumulate on capacitor C0 while transistor Q0 is off, but will be output quickly once transistor Q0 is turned on by actuation of the push button 314.

Because of the capabilities of conventional 3V button cell batteries, a realistic charging circuit must also limit the current drawn from the battery. Two different ways are provided in accordance with the present invention to achieve this result, taking into consideration the CMOS pin voltages and current limits of the microprocessor.

The first method utilizes an analog limit circuit to limit the current flow. The analog limit circuit preferably includes a control input and a transistor configuration operating in the linear region. This allows the circuit to operate as a constant current source with a very low current to charge the energy storage circuit. However, such an analog limit circuit can be sensitive to temperature extremes that might be encountered during transportation and storage of the delivery device.

The second method of limiting the current employs a charging circuit that will pulse under microprocessor control. A pulsed charging circuit is obtained using transistors operating in the: saturation region with the CMOS level being used to switch the current flow on and off repeatedly. When the current is pulsed fast enough, the average current flow from the battery can be precisely controlled. Because conventional button cell batteries can produce over a milliamp of current in a pulse, this allows a charging circuit to be built with no current limit other than the switching of the charging circuit via the microprocessor.

Once the capacitor C0 is fully charged, the charge level is maintained by providing enough current to overcome the capacitor leakage current. As necessary, the analog current limiting approach or the pulsed approach provides this flow of maintenance current. However, leakage can also be overcome by the battery itself, as by leaving the charge circuit is left enabled.

The microprocessor also controls the discharge of the energy storage capacitor C0 to energize the nitinol wire actuator. This circuit discharges the capacitor C0 into the actuator with as little voltage loss as possible, by minimizing forward bias voltage on the transistor Q0 and lowered series resistance. In addition, the capacitor chosen for the energy store has a very low internal series resistance. The internal resistance of the capacitor and the resistance of the energizing circuit must be negligible with respect to the actuator resistance (which is on the order of only 4 ohms), in order to avoid an undesirable enough loss of power to the actuator.

The control signals from the microprocessor will be 3V CMOS levels that switch the voltage (near 3V) on the capacitor through the actuator. This is achieved with a transistor switching circuit interfaced to the CMOS output of the microcontroller, as shown in FIG. 2. Here, the switching circuit 320 includes a bipolar inverted transistor Q1 322 having its base 324 connected to the input/output 314, it collector 326 connected to ground and its emitter 328 connected to one end of a series circuit of the nitinol wire actuator 330 and the capacitor C0 308, the other end being connected to ground.

As will be apparent to one of ordinary skill in the art, other mechanical arrangements can be adapted to control the timed advancement of the vials with respect to the pump assembly. For example, a clockwork mechanism, powered either by a battery or spring, can be employed in conjunction with the escapement mechanism described above. In this embodiment, a rotating shaft can be provided with a wheel having a cam surface that releases the support member interlock and the support member rotates to position a fresh vial in a ready position relative to the pump assembly. The mechanical clockwork mechanism can also be employed to generate a signal to activate a battery-powered audible signal and/or an LED or other visual signal to alert and indicate to the patient that the dispensing device is ready for use. In order to conserve the motive force, e.g., the battery or coil spring, the clockwork movement can be stopped when a vial reaches the ready position. Upon movement of the pump actuator to drive the plunger into the vial and thereby discharge the liquid pharmaceutical composition, the clock movement can be restarted, as by release of a lever control arm or by virtue of a signal transmitted to the microprocessor, e.g., from a magnetic sensor, a switch or other means known to the art.

Other alternative control means include one or more spring solenoids mounted, e.g., on the support member 40, to position the solenoids moveable member to engage an aperture in a wall of the housing 60 to prevent relative movement between the elements. When the engaged solenoid is temporarily activated, the moveable member is withdrawn from the restraining position in the aperture and relative movement occurs. The same or a second solenoid having an extending spring-loaded moveable member engages in sliding contact until it encounters the same or another spaced aperture which it enters to stop the relative movement and to advance a vial to the ready position.

These and numerous other modifications to the various mechanical and electrical systems will be apparent to one of ordinary skill based on the disclosure contained herein, without departing from the scope and content of the invention as defined by the attached claims.

We claim:

1. A method for controlling the minimum time interval between the self-administration of a plurality of prescribed unit doses of an intranasal pharmaceutical composition intranasally by a patient capable of self-administering the composition, the method comprising:
   a) providing a plurality of sealed vials, each vial having an access orifice and containing the prescribed unit dose of the pharmaceutical composition;
   b) providing a drug delivery device having a microprocessor, a power source, and means for securing a plurality of the sealed vials containing the pharmaceutical composition in a predetermined array and dispensing means for recovering the pharmaceutical composition from each of the vials and dispensing the pharmaceutical composition in the form of a spray for intranasal administration in response to a manual activation force applied to the drug delivery device by the patient;
   c) securing a plurality of the sealed vials to a supporting member rotatably mounted in the drug delivery device in the predetermined array;
   d) programming the microprocessor to generate a signal at the end of a prescribed period of time following the dispensing of a dose of pharmaceutical composition from a vial;
   e) generating a signal to initiate sequential movement of the vials relative to the dispensing means; and
   f) sequentially moving each of the vials containing the pharmaceutical composition relative to the dispensing means at the end of a prescribed time interval following activation of the dispensing means to intranasally administer a dose of the liquid composition.

2. The method of claim 1, wherein the prescribed time interval between each sequential movement is the same.

3. The method of claim 1, wherein each of the sequential movements occur in the range of from 2 to 4 hours.

4. The method of claim 1 which includes generating an audible or visual signal at the end of the prescribed time interval.

5. The method of claim 1, wherein a motive force for moving the vials is applied continuously to the rotatably mounted support member and the rotation of the support member is restrained by control means.

6. The method of claim 5 which includes the step of periodically moving the control means in response to the microprocessor signal, whereby the vials are rotationally moved in response to the motive force.

7. The method of claim 5, wherein the control means moves between first and second restraining positions with respect to said support member, and the method includes sequentially moving the control member between the first and second restraining positions to control the sequential movement of the vials.

8. The method of claim 5 which includes the steps of charging and then discharging a capacitor to thereby generate a current in response to signals received from the microprocessor.

9. The method of claim 8, wherein the current discharged from the capacitor is passed through a shape memory actuated wire operatively joined to said control means.

10. The method of claim 1, wherein each of the sequential movements is performed by a patient after the signal is generated.

11. The method of claim 1, wherein each of the sequential movements is performed by a motive force generated from the device after the signal is generated.

12. An apparatus for the intranasal administration of a plurality of doses of a liquid pharmaceutical composition, the apparatus comprising:
   a) a plurality of sealed vials, each vial having an access orifice and containing a predetermined volume of the pharmaceutical composition;
   b) a vial supporting member having supports for receiving the plurality of sealed vials;
   c) a pump assembly including a liquid delivery channel for conveying the liquid pharmaceutical composition from the interior of the vial to a discharge outlet;
   d) a pump activator cooperating with said pump assembly;

e) means for sequentially aligning the pump assembly with the access orifice of each of the vials to permit discharge of the liquid pharmaceutical composition from the aligned vial upon actuation of the pump;

f) an ergonomic intranasal cap affixed to said pump assembly and in communication with said pump assembly discharge outlet;

g) motive means for moving the vial support member relative to the pump assembly;

h) release means for restricting the movement of the vial support member relative to the pump assembly; and i) a programmable control means for controlling the release means, whereby the support member advances a vial containing pharmaceutical composition into alignment with the pump assembly for discharging the pharmaceutical composition upon activation of the pump actuator.

13. The apparatus of claim 12 where the release means comprises an escapement assembly.

14. The apparatus of claim 13 where the release means include a nitinol wire and an electrical discharge circuit, whereby an electric current is passed through said nitinol wire in response to a signal generated by said programmable control means.

15. The apparatus of claim 12 where the means for moving the vial support member is selected from the group consisting of springs, electric motors, elastic members and manually applied forces.

16. The apparatus of claim 12 where the intranasal cap includes an atomizing chamber, whereby a liquid discharged from the cap is in the form of a spray.

17. The apparatus of claim 12 where the vial support member is generally circular and each of the plurality of supports is positioned to receive a vial radially with the vial access orifice facing outwardly.

18. The apparatus of claim 17 where the vial support member includes at least one central chamber and the programmable control means is contained in the at least one central chamber.

19. The apparatus of claim 18 which further includes a power source.

20. The apparatus of claim 19 where the power source is at least one battery.

21. The apparatus of claim 12 which contains at least twelve vials.

22. The apparatus of claim 12 where each of the plurality of vials contains a unit dose of the pharmaceutical composition.

23. The apparatus of claim 12 where the release means further includes a ratchet assembly, whereby the vial support member is movable in only one direction relative to the pump assembly.

24. The apparatus of claim 23 where a pawl of the ratchet assembly is fixed relative to the vial support member.

25. An apparatus for the intranasal administration of a plurality of predetermined unit doses of a liquid pharmaceutical composition, each of said unit doses being contained in a plurality of sealed vials of uniform dimension, said apparatus comprising:

a) a vial supporting member for receiving the plurality of sealed vials each of said vials having an access orifice;

b) a pump assembly including a liquid delivery channel for conveying the liquid pharmaceutical composition from the interior of a vial to a discharge outlet;

c) a pump activator cooperating with said pump assembly d) means for aligning the pump assembly and the access orifice of each of the vials to permit discharge of the liquid pharmaceutical composition from the aligned vial upon activation of the pump;

e) an ergonomic intranasal cap affixed to said pump assembly and in communication with said pump assembly discharge outlet;

f) motive means for moving the vial support member relative to the pump assembly;

g) release means for restricting the movement of the vial support member relative to the pump assembly; and h) a preprogrammed microprocessor for controlling the release means, whereby the support member advances a vial containing pharmaceutical composition into alignment for discharging the pharmaceutical composition upon activation of the pump actuator in response to a signal from the microprocessor.

26. The apparatus of claim 25, wherein both of the timing means and the control means are elements of a programmable microprocessor.

27. The apparatus of claim 25 that includes a plurality of button cell batteries.

28. The apparatus of claim 25, wherein the release means includes a solenoid.

29. The apparatus of claim 25 that includes at least one housing member that engages the supporting member; whereby the plurality of vials is contained between the housing and support member.

30. The apparatus of claim 29 comprising a pair of mating housing members that enclose the support member.

31. The apparatus of claim 30 that includes an aperture in said mated housing, whereby a manual force can be applied to the periphery of the enclosed support member.

32. The apparatus of claim 29, wherein the pump assembly extends from and is joined to at least one housing member.

33. The apparatus of claim 25, wherein the microprocessor has at least one pin voltage and wherein the control means includes an actuator for actuating the rotating means, the actuator being powered by the at least one pin voltage.

34. The apparatus of claim 33, wherein the actuator is a nitinol wire.

35. The apparatus of claim 34, wherein the control—means includes a capacitor charging circuit chargeable by the at least one pin voltage, the actuator being powered by discharge of the capacitor charging circuit.

36. The apparatus of claim 33, wherein, the control means includes a manually actuated input means, the control means actuating the rotating means in response to manual actuation of the input means at one of the prescribed times for delivery of a drug dosage determined by the timing means.

37. The apparatus of claim 36, wherein the actuator is a nitinol wire.

38. The apparatus of claim 37, wherein the control means includes a capacitor charging circuit chargeable by the at least one pin voltage, the actuator being powered by discharge of the capacitor charging circuit in response to manual actuation of the input means.

39. The apparatus of claim 25, that includes a button cell battery for providing power for actuating the rotating means.

40. The apparatus of claim 39, wherein the programmable microprocessor is powered by the battery, the microprocessor having at least one pin voltage in response to power from the battery.

41. The apparatus of claim 40, wherein the actuator is a nitinol wire.

42. The apparatus of claim 41, wherein the control means includes a capacitor charging circuit chargeable by the at least one pin voltage, the actuator being powered by discharge of the capacitor charging circuit.

43. The apparatus of claim 40, wherein the control means includes a manually actuated input means, the control means actuating the rotating means in response to manual actuation of the input means at one of the prescribed times for delivery of a drug dosage determined by the timing means.

44. The apparatus of claim 43, wherein the actuator is a nitinol wire.

45. The apparatus of claim 44, wherein the control means includes a capacitor charging circuit chargeable by the at least one pin voltage, the actuation being powered by discharge of the capacitor charging circuit in response to manual actuation of the input means.

46. The apparatus of claim 25, wherein each of the plurality of vials is independently supported.

47. The apparatus of claim 46, wherein each vial is generally cylindrical and is received in a supporting snap-fit.

* * * * *